(12) United States Patent
Hutchison, III et al.

(10) Patent No.: US 10,818,378 B2
(45) Date of Patent: Oct. 27, 2020

(54) ENCODING TEXT INTO NUCLEIC ACID SEQUENCES

(71) Applicant: Codex DNA, Inc., San Diego, CA (US)

(72) Inventors: Clyde A. Hutchison, III, San Diego, CA (US); Michael G. Montague, Montgomery Village, MD (US); Hamilton O. Smith, San Diego, CA (US)

(73) Assignee: Codex DNA, Inc., San Diego, CA (US)

( * ) Notice: Subject to any disclaimer, the term of this patent is extended or adjusted under 35 U.S.C. 154(b) by 553 days.

(21) Appl. No.: 15/052,781

(22) Filed: Feb. 24, 2016

(65) Prior Publication Data

US 2016/0168579 A1 Jun. 16, 2016

Related U.S. Application Data

(63) Continuation of application No. 12/916,344, filed on Oct. 29, 2010, now abandoned, and a continuation of application No. 12/783,489, filed on May 19, 2010, now Pat. No. 9,267,132.

(60) Provisional application No. 61/256,913, filed on Oct. 30, 2009.

(51) Int. Cl.
*G16B 30/00* (2019.01)
*C12Q 1/68* (2018.01)

(52) U.S. Cl.
CPC ............... *G16B 30/00* (2019.02); *C12Q 1/68* (2013.01)

(58) Field of Classification Search
CPC .......................... C12Q 2563/185; G16B 30/00
See application file for complete search history.

(56) References Cited

U.S. PATENT DOCUMENTS

| | | | |
|---|---|---|---|
| 6,175,830 B1 | 1/2001 | Maynard | |
| 6,261,807 B1 | 7/2001 | Crouzet et al. | |
| 6,312,911 B1 | 11/2001 | Bancroft et al. | |
| 6,607,878 B2 | 8/2003 | Sorge | |
| 7,056,724 B2 | 6/2006 | Wong et al. | |
| 7,323,307 B2 | 1/2008 | Lockhart et al. | |
| 2003/0219756 A1 | 11/2003 | Wong et al. | |
| 2005/0026164 A1 | 2/2005 | Zhou | |
| 2006/0014169 A1 | 1/2006 | Fiandt et al. | |
| 2006/0024811 A1 | 2/2006 | Wong et al. | |
| 2006/0269939 A1 | 11/2006 | Singh et al. | |
| 2007/0031850 A1 | 2/2007 | Mounts et al. | |
| 2007/0042372 A1 | 2/2007 | Arita | |
| 2007/0048756 A1 | 3/2007 | Mei et al. | |
| 2007/0264688 A1 | 11/2007 | Venter et al. | |
| 2007/0269862 A1 | 11/2007 | Glass et al. | |
| 2008/0124725 A1 | 5/2008 | Barrangou et al. | |
| 2008/0125583 A1 | 5/2008 | Rigoutsos et al. | |
| 2011/0040488 A1 | 2/2011 | Singh et al. | |

FOREIGN PATENT DOCUMENTS

| | | |
|---|---|---|
| AU | 2002325859 B2 | 5/2008 |
| WO | WO 2002/079481 A1 | 10/2002 |
| WO | WO 2003/048346 A1 | 6/2003 |
| WO | WO 2006/110680 A1 | 10/2006 |
| WO | WO 2008/016380 A2 | 2/2008 |
| WO | WO 2008/024129 A2 | 2/2008 |
| WO | WO 2008/144192 A1 | 11/2008 |
| WO | WO 2009/048885 A2 | 4/2009 |
| WO | WO 2009/134814 A2 | 11/2009 |
| WO | WO 2010/0102257 A2 | 9/2010 |

OTHER PUBLICATIONS

Ludwig, W. et al. ARB: a software environment for sequence data. Nucleic Acids Research 32, 1363-1371 (2004).*
Six tables of English-language letter frequency estimates, retrieved by the examiner from the Internet on Oct. 8, 2018.*
Arita et al., "Secret Signatures Inside Genomic DNA", Biotechnol. Prog. 20:1605-1607, 2004.
Australian Examination Report dated Jun. 1, 2015 regarding AU 201313247.
Benders et al.: "Cloning whole bacterial genomes in yeast", *Nucleic Acids Res.*, May 2010; 38(8):2558-2569. Epub. Mar. 7, 2010.
Bheemanaik et al.: "Structure, function and mechanism of exocyclic DNA methyltransferases", Biochem. J., 399(2):177-190 (2006).
Bolsover, S. R. et al: "Cell Biology: A Short Course"; (John Wiley & Sons, Inc.: Hoboken, NJ, USA, 2004) Excerpt of pp. 11-12 and 105-125.
Clelland et al.: "Hiding messages in DNA microdots", Nature, 399(6736):533-534 (1999).
European Search Report dated Mar. 1, 2013 regarding EP 108 27 576.9.
Gibson et al.: "Complete chemical synthesis, assembly, and cloning of a Mycoplasma genitalium genome", Science, Feb. 29, 2008; 319(5867):1215-1220. Epub. Jan. 24, 2008.
Gibson et al.: "One-step assembly in yeast of 25 overlapping DNA fragments to form a complete synthetic Mycoplasma genitalium genome", Proc. Natl. Acad. Sci. U.S.A., Dec. 23, 2008;105(51):20404-20409. Epub. Dec. 10, 2008.
Gordon et al.: "Mechanisms of Chromosome Number Evolution in Yeast"; PLoS Genetics 7(7):1-13, 2011.

(Continued)

*Primary Examiner* — Soren Harward
(74) *Attorney, Agent, or Firm* — DLA Piper LLP (US)

(57) ABSTRACT

Methods and apparatus are disclosed herein for encoding human readable text conveying a non-genetic message into nucleic acid sequences with a substantially reduced probability of biological impact and decoding such text from nucleic acid sequences. In one embodiment, each symbol of a symbol set of human readable symbols uniquely maps to a respective codon identifier. Mapping may ensure that each symbol will not map to a codon identifier that generates an amino acid residue which has a single-letter abbreviation that is the equivalent to the respective symbol. Synthetic nucleic acid sequences comprising such human readable text, and recombinant or synthetic cells comprising such sequences are provided, as well as methods of identifying cells, organisms, or samples containing such sequences.

7 Claims, 12 Drawing Sheets
Specification includes a Sequence Listing.

(56) References Cited

OTHER PUBLICATIONS

Heider et al.: "*DNA watermarks: A proof of concept*", BMC Molec. Biol., 9:40, 2008.
Heider et al.: "*DNA-based watermarks using the DNA-Crypt algorithm*", BMC Bioinformatics, 8:176, 2007.
Huadong Pei et al.: "*FKBP51 Affects Cancer Cell Response to Chemotherapy by Negatively Regulating Akt*"; Cancer Cell, Sep. 1, 2009, 16:3; 259-266.
International Search Reports (ISR) from PCT/US2010/54862.
Kouprina, N. et al.: "*Rescue of targeted regions of mammalian chromosomes by in vivo recombination in yeast*"; Genome Research, 8:1, Jun. 1998, pp. 666-672.
Kouprina et al.: "*Selective isolation of large chromosomal regions by transformation-associated recombination cloning for structural and functional analysis of mammalian genomes*", Methods Mol. Biol., 349:85-101 (2006).
Kouprina, N. et al.: "*Construction of Human Chromosome 16- and 5-Specific Circular YAC/BAC Libraries by in Vivo Recombination in Yeast (TAR Cloning)*"; Genomics, 53:1, Oct. 1, 1998, pp. 21-28.
Lartigue et al.: "*Genome transplantation in bacteria: changing one species to another*", Science, Aug. 3, 2007; 317(5838):632-638. Epub. Jun. 28, 2007.
Lartigue et al: "*Creating Bacterial Strains From Genomes That Have Been Cloned and Engineered in Yeast*", Science; Sep. 25, 2009, vol. 325, pp. 1693-1696.
Leier et al.: "*Cryptography with DNA binary strands*", Biosystems 57:13-22, 2000.
Maloy, S: "*Bacterial Chromosomes*"; SDSU Microbial Genetics, Jul. 12, 2002. 4 pages http://www.sci.sdsu.eduhsmaloy/MicrobialGenetics/topics/chroms-genes-prots/chromosomes.html;.
Marillonnet, Sylvestre et al.: "*Encoding technical information in GM organisms.*", Nature Biotech; Mar. 3, 2003, vol. 21:3 pp. 224-226.
Naylor, Margaret: *Chromosome Numbers in the Algae*; British Phycological Bulletin 1(6): 34-40, 1958.
Noskov et al.: "*A general cloning system to selectively isolate any eukaryotic or prokaryotic genomic region in yeast*", BMC Genomics, Apr. 29, 2003; 4(1):16. Epub. Apr. 29, 2003.
Pennisi E.: "*Genetics. Replacement genome gives microbe new identity*", Science, 316(5833):1827 (2007).
Smith, Geoff C. et al.: "*Some possible codes for encrypting data in DNA.*"; Biotech Letters, vol. 25:14, Jul. 2003, pp. 1125-1133.
Strathern, Jeffrey N. et al.: "*Recovery of Plasmids from Yeast into Escherichia coli: Shuttle Vectors*"; Methods in Enzymol. 194:319-329, 1991.
Wieloch, Wioletta: "*Chromosome visualization in filamentous fungi*" J. Microbiological Methods, 67:1-8, 2006.
Wikipedia: "*List of Organisms by Chromosome Count*"; Wikipedia; Mar. 24, 2013, 10 pages. Retrieved from "http://en.wikipedia.org/w/index.php?;title=List of organisms by chromosome count&oldid=546806158", Categories: Classical genetics Biology-related lists.
Zhou, Fuchun et al.: "*A sequence-independent in vitro transposon-based strategy for* efficient *cloning of genomes of large DNA viruses as bacterial artificial chromosomes*"; Nucleic Acids Research, 37:1, Jan. 2009.

\* cited by examiner

Symbol Map 220

| GGA = " | GAA = ' | TTC = # | CAG = : | TGT = ; | ACG = [ |
|---|---|---|---|---|---|
| AGG = ] | AAA = { | AAG = } | CCG = ( | GAC = ) | CGG = < |
| AGC = > | CAC = / | CTC = \ | CGA = . | GTG = , | CCC = - |
| CCT = + | CCA = = | TCG = @ | ATC = $ | GAT = % | GAG = ! |
| ACC = & | ATG = * | ATA = space | GGG = new line | | |
| | | | | | |
| TCT = 0 | CTT = 1 | ACT = 2 | AAT = 3 | AGA = 4 | GCG = 5 |
| GCC = 6 | TAT = 7 | CGC = 8 | GTA = 9 | | |
| | | | | | |
| TAG = A | AGT = B | TTT = C | ATT = D | TAA = E | GGC = F |
| TAC = G | TCA = H | CTG = I | GTT = J | GCA = K | AAC = L |
| CAA = M | TGC = N | CGT = O | ACA = P | TTA = Q | CTA = R |
| GCT = S | TGA = T | TCC = U | TTG = V | GTC = W | GGT = X |
| CAT = Y | TGG = Z | | | | |

Codon identifiers 302

Symbols 304

FIG. 3

Alt Full-Monty-Code

|  |  | 2nd Base in Full-Monty-Code | | | | |
|---|---|---|---|---|---|---|
|  |  | T | C | A | G |  |
| 1st Base in Full-Monty-Code | T | tab |  |  |  | T |
|  |  |  |  |  |  | C |
|  |  |  |  |  |  | A |
|  |  |  |  |  |  | G |
|  | C |  |  |  |  | T |
|  |  |  |  |  |  | C |
|  |  |  |  |  |  | A |
|  |  |  |  |  |  | G |
|  | A |  |  |  |  | T |
|  |  |  |  |  |  | C |
|  |  | space |  |  |  | A |
|  |  |  |  |  |  | G |
|  | G |  |  | SHIFT |  | T |
|  |  |  |  | CTRL |  | C |
|  |  |  |  | ALT |  | A |
|  |  |  |  | LOCK | new-line | G |

3rd Base in Full-Monty-Code

FIG. 8A

Ctrl Full-Monty-Code

| | | 2nd Base in Full-Monty-Code | | | | |
|---|---|---|---|---|---|---|
| | | T | C | A | G | |
| 1st Base in Full-Monty-Code | T | tab | | | | T |
| | | | | | | C |
| | | | | | | A |
| | | | | | | G |
| | C | | | | | T |
| | | | | | | C |
| | | | | | | A |
| | | | | | | G |
| | A | | | | | T |
| | | | | | | C |
| | | space | | | | A |
| | | | | | | G |
| | G | | | SHIFT | | T |
| | | | | CTRL | | C |
| | | | | ALT | | A |
| | | | | LOCK | new-line | G |

3rd Base in Full-Monty-Code

FIG. 8B

Default Full-Monty-Code

| 1st Base | | 2nd Base in Full-Monty-Code | | | | 3rd Base |
|---|---|---|---|---|---|---|
| | | T | C | A | G | |
| T | | c | 0 | 7 | ; | T |
| | | tab | u | g | n | C |
| | | q | h | e | t | A |
| | | v | | a | z | G |
| C | | 1 | ' | y | o | T |
| | | \ | - | / | 8 | C |
| | | r | = | m | . | A |
| | | | | | | G |
| A | | d | 2 | 3 | b | T |
| | | $ | & | 1 | | C |
| | | space | p | | 4 | A |
| | | | [ | | ] | G |
| G | | j | s | SHIFT | x | T |
| | | w | 6 | CTRL | f | C |
| | | 9 | k | ALT | | A |
| | | , | 5 | LOCK | new-line | G |

FIG. 8C

Shift Full-Monty-Code

| | | 2nd Base in Full-Monty-Code | | | | |
|---|---|---|---|---|---|---|
| | | T | C | A | G | |
| 1st Base in Full-Monty-Code | T | C | ) | & | : | T |
| | | tab | U | G | N | C |
| | | Q | H | E | T | A |
| | | V | | A | Z | G |
| | C | ! | " | Y | O | T |
| | | \| | – | ? | * | C |
| | | R | + | M | > | A |
| | | | | | | G |
| | A | D | @ | # | B | T |
| | | $ | & | L | | C |
| | | space | P | | $ | A |
| | | | { | | } | G |
| | G | J | S | SHIFT | X | T |
| | | W | ^ | CTRL | F | C |
| | | ( | K | ALT | | A |
| | | < | % | LOCK | new-line | G |

(3rd Base in Full-Monty-Code)

FIG. 8D

Monty Code

| | | 2nd Base in Full-Monty-Code | | | | |
|---|---|---|---|---|---|---|
| | | T | C | A | G | |
| | T | C | O | 7 | ; | T |
| | | # | U | G | N | C |
| | | Q | H | E | T | A |
| | | V | @ | A | Z | G |
| | C | 1 | + | Y | O | T |
| | | \ | - | / | 8 | C |
| | | R | = | M | . | A |
| | | I | ) | : | < | G |
| | A | D | 2 | 3 | B | T |
| | | $ | & | L | > | C |
| | | space | P | { | 4 | A |
| | | * | [ | } | ] | G |
| | G | J | S | % | X | T |
| | | W | 6 | ( | F | C |
| | | 9 | K | ' | " | A |
| | | , | 5 | ! | new-line | G |

1st Base in Full-Monty-Code (left axis)     3rd Base in Full-Monty-Code (right axis)

FIG. 8E

SEQUENCE LISTING

```
<160> NUMBER OF SEQ ID NOS: 17

<210> SEQ ID NO 1
<211> LENGTH: 12
<212> TYPE: DNA
<213> ORGANISM: Artificial sequence
<220> FEATURE:
<223> OTHER INFORMATION: Synthetic construct: all-6 reading frame stop
      codon containing sequence

<400> SEQUENCE: 1
ttaactagct aa                                                   12

<210> SEQ ID NO 2
```

-continued

```
<211> LENGTH: 11
<212> TYPE: DNA
<213> ORGANISM: Artificial sequence
<220> FEATURE:
<223> OTHER INFORMATION: Synthetic construct: 5 prime reading frame

<400> SEQUENCE: 2
taactagcta a                                                          11

<210> SEQ ID NO 3
<211> LENGTH: 10
<212> TYPE: DNA
<213> ORGANISM: Artificial sequence
<220> FEATURE:
<223> OTHER INFORMATION: Synthetic construct: 5 prime reading frame

<400> SEQUENCE: 3
aactagctaa                                                            10

<210> SEQ ID NO 4
<211> LENGTH: 12
<212> TYPE: DNA
<213> ORGANISM: Artificial sequence
<220> FEATURE:
<223> OTHER INFORMATION: Synthetic construct: 3 prime reading frame

<400> SEQUENCE: 4
ttagctagtt aa                                                         12

<210> SEQ ID NO 5
<211> LENGTH: 11
<212> TYPE: DNA
<213> ORGANISM: Artificial sequence
<220> FEATURE:
<223> OTHER INFORMATION: Synthetic construct: 3 prime reading frame

<400> SEQUENCE: 5
tagctagtta a                                                          11

<210> SEQ ID NO 6
<211> LENGTH: 10
<212> TYPE: DNA
<213> ORGANISM: Artificial sequence
<220> FEATURE:
<223> OTHER INFORMATION: Synthetic construct: 3 prime reading frame

<400> SEQUENCE: 6
acgtagttaa                                                            10

<210> SEQ ID NO 7
<211> LENGTH: 15
<212> TYPE: DNA
<213> ORGANISM: Artificial sequence
<220> FEATURE:
<223> OTHER INFORMATION: Synthetic construct: partial watermark

<400> SEQUENCE: 7
ttaactagct aagtt                                                      15

<210> SEQ ID NO 8
<211> LENGTH: 18
<212> TYPE: DNA
<213> ORGANISM: Artificial sequence
<220> FEATURE:
<223> OTHER INFORMATION: Synthetic construct: partial watermark

<400> SEQUENCE: 8
```

```
ttaactagct aagttttt                                              18
```

<210> SEQ ID NO 9
<211> LENGTH: 156
<212> TYPE: DNA
<213> ORGANISM: Artificial sequence
<220> FEATURE:
<223> OTHER INFORMATION: Synthetic construct: watermark with flanking
     all 6 stop codons

<400> SEQUENCE: 9

```
ttaactagct aagttttttt gctgcccgct tgactatagc tgtgcatatc tcttactcga    60
aatatataga acaacatact actgtactca tgagctatac tataagctta actattgtaa   120
attgtgataa cttcttctgt acgattaact agctaa                             156
```

<210> SEQ ID NO 10
<211> LENGTH: 132
<212> TYPE: DNA
<213> ORGANISM: Artificial sequence
<220> FEATURE:
<223> OTHER INFORMATION: Synthetic construct: watermark

<400> SEQUENCE: 10

```
gttttttgc tgcccgcttg actatagctg tgcatatctc ttactcgaaa tatatagaac    60
aacatactac tgtactcatg agctatacta taagcttaac tattgtaaat tgtgataact   120
tcttctgtac ga                                                       132
```

<210> SEQ ID NO 11
<211> LENGTH: 18
<212> TYPE: DNA
<213> ORGANISM: Artificial sequence
<220> FEATURE:
<223> OTHER INFORMATION: Synthetic construct: 5 prime reading frame

<400> SEQUENCE: 11

```
gttttttgc tgcccgct                                              18
```

<210> SEQ ID NO 12
<211> LENGTH: 18
<212> TYPE: DNA
<213> ORGANISM: Artificial sequence
<220> FEATURE:
<223> OTHER INFORMATION: Synthetic construct: 5 prime reading frame

<400> SEQUENCE: 12

```
tttttttgct gcccgctt                                              18
```

<210> SEQ ID NO 13
<211> LENGTH: 18
<212> TYPE: DNA
<213> ORGANISM: Artificial sequence
<220> FEATURE:
<223> OTHER INFORMATION: Synthetic construct: 5 prime reading frame

<400> SEQUENCE: 13

```
tttttttgctg cccgcttg                                              18
```

<210> SEQ ID NO 14
<211> LENGTH: 1062
<212> TYPE: DNA
<213> ORGANISM: Artificial sequence
<220> FEATURE:
<223> OTHER INFORMATION: Synthetic construct: Watermark-1

<400> SEQUENCE: 14

```
ttaactagct aagttcgaat atttctatag ctgtacatat tgtaatgctg ataactaata      60
ctgtgcgctt gactgtgatc ctgataaata acttcttctg tagggtagag ttttatttaa     120
ggctactact ggttgcaaac caatgccgta cattactagc ttgatccttg gtcggtcatt     180
gggggatatc tcttactaat agagcggcct atcgcgtatt ctcgccggac ccccctctcc     240
cacaccagcg gtgtacatca ccaagaaaat gaggggaacg gatgaggaac gagtgggggc     300
tcattgctga tcataatgac tgtttatata ctaatgccgt caactgtttg ctgtgatact     360
gtgctttcga gggcgggaga ttcttttttga catacataaa tatcatgaca aacagccgg     420
tcatgacaaa acagccggtc ataatagatt agccggtgac tgtgaaacta aagctactaa     480
tgccgtcaat aaatatgata atagcaacgg cctgactgtg aaactaaagc cggcactcat     540
aatagattag ccggagtcgt attcatagcc ggtagatatc actataaggc ccaggatcat     600
gatgaacaca gcaccacgtc gtcgtccgag ttttttttgcg cgacgtctat accacggaag     660
ctgatcataa atagttttttt tgctgcggca ctagagccgg acaagcacac tacgtttgta     720
aatacatcgt tccgaattgt aaataattta atttcgtatt taaattaatg atcactggct     780
atagtctagt gataactaca atagctagca ataagtcata tataacaata gctgaacctg     840
tgctacatat ccgctatacg gtagatatca ctataaggcc caggacaata gctgactgac     900
gtcagcaact acgtttagct tgactgtggt cggttttttt gctgcgacgt ctatacggaa     960
gctcataact ataagagcgg cactagagcc ggcacacaag ccggcacagt cgtattcata    1020
gccgcactca tgacaaaaca gcggcgcgcc ttaactagct aa                       1062
```

<210> SEQ ID NO 15
<211> LENGTH: 898
<212> TYPE: DNA
<213> ORGANISM: Artificial sequence
<220> FEATURE:
<223> OTHER INFORMATION: Synthetic construct: Watermark-2

<400> SEQUENCE: 15

```
ttaactagct aacaactggc agcataaaac atatagaact acctgctata agtgatacaa      60
ctgttttcat agtaaaacat acaacgttgc tgatagtact cctaagtgat agcttagtgc     120
gtttagctat attgtaggct tcataataag tgatattttta gctacgtaac taaataaact     180
agctatgact gtactcctaa gtgatatttt catcctttgc aatacaataa ctactacatc     240
aatagtgcgt gatatcctgt gctagatata gaacacataa ctacgtttgc tgttttcagt     300
gatatgctag tttcatctat agatataggc tgcttagatt ccctactagc tatttctgta     360
ggtgatatac gtccattgca taattaatgc atttaactag ctgtgatact atagcatccc     420
cattcctagt gcatattttc atcctagtgc tacgtgatat aattgtacta atgcctgtag     480
ataatttaat gcctggctcg tttgtaggtg aaatttagtg cctgtaaaac atatacctga     540
gtgctcgttg cgtgatagtt cgttcatgca tatacaacta ggctgctgtg atatggtcac     600
tgcccttact gtgctacata ttactgcgag ggggatgact ataaacctgt tgtaagtgat     660
atgacgtata taactactag tgatatgacg tataggctag aacaacgtga tatgacgtat     720
atgactactg tcccaaacat cagtgatatg acgtatacta aatttcata atagtgataa     780
ataaacctgg gctaaatacg ttcctgaata cgtggcataa acctgggcta acgaggaata     840
cccatagttt agcaataagc tatagttcgt catttttaag gcgcgcctta actagtaa      898
```

<210> SEQ ID NO 16
<211> LENGTH: 926
<212> TYPE: DNA
<213> ORGANISM: Artificial sequence
<220> FEATURE:
<223> OTHER INFORMATION: Synthetic construct: Watermark-3

<400> SEQUENCE: 16

```
ttaactagct aatttaacca tatttaaata tcatcctgat tttcactggc tcgttgcgtg      60
atatagattc tactgtagtg ctagatagtt ctgtactagg tgatactata gatttcatag     120
atagcacact ggcttcatgc taggcatccc aatagctagt gatagtttag tgcatacaac     180
gtcatgtgat acaacgttgc tggctgtaga tacaacgtcg tattctgtaa gtgatacaat     240
agctattgct gtgcaaggcc tatagtggct gtaactagtg atatcacgta acaaccatat     300
aagttagatt taatgcccct gactgaacgc tcgttgcgtg atagtttagg ctcgttgcat     360
acaactgtga ttttcataaa acacgtgata atttagtgct agataagttc cgcttagcaa     420
gtgatagttt ccgcttgact gtgcatagtt cgttcatgcg ctcgttgcgt gataaactag     480
gcagcttcac aactgataat ttaattgctg aattgctggc tgtctagtgc tagtgatcat     540
agtgcgtgat agtttaagct gctctgtttt agatatcacg tgcttgataa tgaaactaac     600
tagtgatact acgtagttaa ctatgaatag gcctactgta attcaatagt gcgtgatatt     660
gaactagatt ctgcaactgc taatatgccg tgctgcacgt ttggtgatag tttagcatgc     720
ttcactataa taaatatggt agttgtaact actgcgaata gggggagtta ataaatatga     780
tcactgtgct acgctatatg ccgttgaata taggctatat gatcataaca tatatagcta     840
taagtgataa gttcctgaat ataggctata tgatcataac atatacaact gtactatgaa     900
taagttaacg aggattaact agctaa                                          926
```

<210> SEQ ID NO 17
<211> LENGTH: 1038
<212> TYPE: DNA
<213> ORGANISM: Artificial sequence
<220> FEATURE:
<223> OTHER INFORMATION: Synthetic construct: Watermark-4

<400> SEQUENCE: 17

```
ttaactagct aatttcattg ctgatcactg tagatatagt gcattctata agtcgctccc      60
acaggctagt gctgcgcacg tttttcagtg atattatcct agtgctacat aacatcatag     120
tgcgtgaaaa cctgatacaa taggtgatat catagcaact gaactgacgt tgcatagctc     180
aactgtgatc agtgatatag attctgatac tatagcaacg ttgcgtgata ttttcactac     240
tggcttgact gtagtcatat gatagtacgt ctaactagca taactagtga tagttatatt     300
tctatagctg tacatattgt aatgctgata actagtgata taatccaact agatagtcct     360
gaactgatcc ctatgctaac taggataaac taactgatac atcgttcctg ctacgtgata     420
gcttcactga gttccataca tcgtcgtgct taaacatcag tgataacact atagagttca     480
tagatactgc attaactagt gatatgactg caatagcttg acgttttgca gtctaaaaca     540
acgtgataat tctgtagtgc tagatactat agatttcctg ctaagtgata agtctactga     600
tttactaatg aatagcttgg ttttggcata cactgtgcgt gcactggtga tagcttttcg     660
ttgatgaata atttccctag cactgtgcgt gatatgctag attctgtaga taggctaaat     720
tcgtctacgt ttgtaggtga tagtttagtt gctgtaacta atattatcct gtgccgttgc     780
taagctgtga tatcatagtg ctgctagata tgataagcaa actaatagag tcgaggggga     840
```

-continued

```
gtctcatagt gaatactgat attttagtgc tgccgttgaa taagttccct gaacatgtga        900
tactgatatt ttagtgctgc cgttgaatat cctgcattta actagcttga tagtgcattc        960
gaggaatacc catactactg ttttcatagc taattatagg ctaacattgc caatagtgcg       1020
gcggccttaa ctagctaa                                                     1038
```

ENCODING TEXT INTO NUCLEIC ACID SEQUENCES

CROSS-REFERENCES TO RELATED APPLICATIONS

This application is a continuation of application Ser. No. 12/916,344, filed Oct. 29, 2010, and claims the benefit of U.S. provisional patent application 61/256,913, filed Oct. 30, 2009, and to U.S. application Ser. No. 12/783,489, filed May 19, 2010, each of which is incorporated by reference in its entirety.

FIELD OF THE INVENTION

The presently disclosed application relates generally to the field of molecular biology. More specifically, this application relates to synthetic nucleic acid sequences comprising non-genetic information.

REFERENCE TO SEQUENCE LISTING

This application contains references to amino acid sequences and/or nucleic acid sequences which have been submitted concurrently herewith as the sequence listing text file "SGI1450-1_ST25.txt", file size 09.02 KiloBytes (KB), created on Oct. 29, 2010. The aforementioned sequence listing is hereby incorporated by reference in its entirety pursuant to 37 C.F.R. § 1.52(e)(5).

BACKGROUND OF THE INVENTION

Biological organisms comprise nucleic acid sequences that encode, among other things, genes that can be used to catalyze chemical reactions within the organism. Genes encompass a number of different regions, such as promoters, terminators, and perhaps most importantly, the open reading frame or coding region of the gene that contains the "text" for the protein of interest. Deoxynucleic acid sequences are transcribed to messenger RNA (mRNA) which is then translated into a protein sequence of interest. There are four bases used in deoxyribonucleic acid sequences, each of which can be used in three positions in a codon and, thus, there are in theory 64 possible codon permutations.

Because many cells have the ability to absorb and retain nucleic acid sequences, some have considered the prospect of using a biological organism as a memory source for storing human readable information. In order to achieve this end, various encoding schemes have been developed which attempt to map human readable symbols into nucleic acid sequences that can be stored within a living organism.

U.S. Pat. No. 6,312,911 discloses a steganographic method for creation of a secret code by producing a DNA molecule comprising a secret message DNA sequence flanked on each side by a primer sequence.

U.S. Pat. No. 7,056,724 discloses a method of storing data in *Deinococcus radians* by performing an evaluation of the genome of *D. radians* relative to one or more criteria for use as a storage medium, preparing a code based on the evaluation, encoding a DNA sequence in accordance to the code to represent the data, and incorporating the encoded DNA sequence into *D. radians*.

U.S. Published Application No. 20080124725 discloses a method of tagging a bacterium by exposing a portion of a CRISPR locus to at least one exogenous nucleic acid sequence to produce at least one tagged bacterium comprising a modified CRISPR locus.

U.S. Pat. No. 6,175,830 discloses a method for generating a searchable informational resource by assigning a categorical tag to each of a plurality of finite elements and arranging the results of a searchable step into a hierarchal structure according to information in categorical tags assigned to finite elements corresponding to searchable database records identified by searching.

U.S. Pat. No. 7,323,307 discloses a method for analyzing mRNA having one or more exons having an order defined by one or more signature sequences, by hybridizing labeled fragments to a nucleic acid array and determining the identity of sequence signatures and the order of one or more exons.

U.S. Pat. No. 6,607,878 discloses a composition of a mixture of different species of molecules, where at least some of the molecules are derived from a combinatorial synthesis process and some species are linked to a tag of linked information encoding elements, and where the physical property of the combination of elements identifies the species of molecule without determining the physical property of each element of the tag and, further, where the tags do not consist solely of nucleotides.

Clelland et al. (*Nature*, volume 399, pages 533-534 (1999)) discloses concealing secret messages hidden in DNA microdots where the messages are flanked by PCR primer sequences.

Heider and Barnekow (*BMC Molec. Biol.*, 9: 40 (2008) and Heider and Barnekow (*BMC Bioinformatics*, 8:176 (2007)) each disclose the application of watermarks based on DNA sequences using a binary code of the numbers 0 and 1.

Leier et al. (*Biosystems*, 57: 13-22 (2000)) disclose two different cryptographic techniques, each of which requires binary codes of the numbers 0 and 1.

Arita and Ohashi (*Biotechnol. Prog.* 20: 1605-1607 (2004)) disclose an encoding scheme in which the actual sequence of the gene that encodes the message is not independent of the genetic code of the organism; the correct decoding of an embedded sequence requires outside knowledge of the wild-type sequence of a carrier gene; and a minimum of 18 nucleotides is required to encode a single letter.

Unfortunately, conventional encoding schemes suffer from a one of two serious drawbacks, either they run the risk of causing a negative biological impact on a cell harboring nucleic acid sequences made using such encoding schemes, or they rely upon codon-redundancy in a carrier-gene of known function. Methods using a carrier-gene are characterized by extreme inefficiency of encoded information and are further limited by their requirement of encoding a message inside a carrier gene of known sequence and limited length. This imposes a limit on the length of the message that can be encoded that is further exacerbated by the inefficiency of the encoding scheme.

SUMMARY OF THE INVENTION

The present application is directed to generating an encoding scheme configured to translate human readable symbols into codon identifiers (i.e., discrete sequences of preferably three elements, where each element contains one of four selected nucleotide bases). In this manner, sequences of human readable symbols can be used to convey non-genetic messages (for example, text messages, trademarks, copyright notices, unique identifying information, etc.) by encoding the message into sequences of codon identifiers. These sequences of codon identifiers may then be used to generate synthetic nucleic acid sequences that are introduced into a living cell or organism as free DNA or incorporated into other various types of cellular nucleic acid materials (e.g., plasmids, chromosomes, mitochondrial DNA, genomes, etc.). The resulting set of codons or codon identifiers effectively serves as a memory source for the encoded sequences of human readable symbols.

Unlike conventional methods of encoding such nucleic acid sequences, embodiments described herein utilize an encoding scheme with a remarkably low probability of biological impact. That is to say, a low probability exists that a synthetic nucleic acid sequence created using invention methods and schemes will be transcribed or translated by a cell's internal biological processes. As a result, the non-genetic message created using invention methods and schemes may be innocuously carried and replicated by cells comprising the message, but may be decoded to provide the human readable symbols, i.e., the message carried therein. Advance knowledge of a gene's structure and/or function is not required in order to decode a given sequence of nucleotides. This greatly simplifies the decoding process, enabling a message recipient to decode one or more messages using a simple human readable symbol map.

Also, since the encoding scheme is configured to translate each human readable symbol of an input message into a three-nucleotide codon identifier, efficiency gains are realized over many conventional encoding systems. Therefore, significantly less storage space is required to store an encoded message, both within a cell or a cell within an organism, and within the transcoder itself or the memory of the transcoder itself.

In a first aspect, provided herein is a synthetic nucleic acid sequence, wherein the synthetic nucleic acid sequence comprises one or more codon identifiers corresponding to a set of human readable symbols of a reference language that conveys a non-genetic message, such as a watermark, and further wherein this sequence is not genetically viable and does not have a biological impact upon a recombinant or synthetic cell or virus comprising this sequence.

In preferred embodiments, this sequence cannot be biologically translated into a functional amino acid sequence by the recombinant or synthetic cell or virus and/or this sequence, and/or the one or more codon identifiers do not correspond to sequence of a naturally-occurring gene or other biologically active sequence. Rather, the one or more codon identifiers correspond to one or more letters, one or more numbers, one or more spaces, one or more punctuation marks, one or more mathematical symbols, etc., one or more typographical characters, one or more new lines, or a combination of any thereof and axe preferably are made up of three nucleotides. In one embodiment, the set of human readable symbols comprises a watermark. Watermarks can be used to convey a non-genetic message and may include, but axe not limited to, a copyright notice, a trademark, a company identifier, a name, a phrase, a sentence, a quotation, genetic information, unique identifying information, data, or a combination of any thereof.

The synthetic nucleic acid sequence can further comprise an all-6 reading frame stop codon containing sequence 5' to a first codon identifier in the sequence, an all-6 reading frame stop codon containing sequence 3' to the last codon identifier in the sequence, or both.

In another aspect, provided herein is a recombinant or synthetic organism containing a synthetic nucleic acid sequence as described herein.

In various embodiments, the recombinant or synthetic organism can be a prokaryotic cell, a eukaryotic cell, an archaeal cell or a virus. In certain preferred embodiments, the recombinant cell can be a bacterial cell, a yeast cell, a fungal cell, an algal cell, an animal cell, or a plant cell. In certain embodiments, the set of human readable symbols can be a watermark that allows the authentication or identification of the recombinant or synthetic cell or virus comprising the synthetic nucleic acid sequence containing the watermark, or of an organism comprising such a recombinant or synthetic cell or virus.

In another aspect, provided herein is a method of creating a recombinant or synthetic organism comprising a watermark that conveys a non-genetic message, comprising: generating a nucleic acid sequence comprising a sequence of codon identifiers selected based upon the text of the watermark such that a symbol mapping maps codon identifiers corresponding to start codon(s) to human readable symbols that possess a disproportionally low frequency in the language of the watermark, and maps codon identifiers corresponding to stop codon(s) to human readable symbols that possess a disproportionally high frequency in the language of the watermark; synthesizing this nucleic acid sequence; and introducing this nucleic acid sequence into a recombinant or synthetic organism.

Alternatively, provided herein is a method of creating a recombinant or synthetic organism comprising a watermark that conveys a non-genetic message, comprising: generating a nucleic acid sequence comprising one or more codon identifiers from a set of human readable symbols of a reference language comprising said watermark, wherein a symbol mapping is configured to map a human readable symbol with a frequency of distribution of less than one percent in the set of human readable symbols to a start codon, and wherein the symbol mapping is further configured to map a human readable symbol with a frequency of distribution of more than five percent in the set of human readable symbols to a stop codon; synthesizing this nucleic acid sequence; and introducing this nucleic acid sequence into a recombinant or synthetic organism.

In preferred embodiments, the symbol mapping does not map a three nucleotide codon identifier to a single letter representation of an amino acid residue normally assigned to that three nucleotide codon in the standard genetic code. In certain embodiments, the generating step is computer-assisted and comprises identifying the set of human readable symbols at a memory module and for each human readable symbol in the set, using a processor to read a symbol mapping for determining a codon identifier which maps to the respective human readable symbol.

A recombinant cell, a synthetic cell, a recombinant virus, a synthetic virus, or a recombinant or synthetic multicellular organism comprising such a non-genetic message can be used for any suitable purpose as is known in the art, for example, in connection with a recombinant plant or crop (e.g., corn, grapes, etc.); a modified animal (e.g., a genetically modified rodent, primate, poultry, large veterinary animal, etc.); a recombinant embryo; a genetically modified organism, cell, cell line or strain; a recombinant organism, cell, cell line or strain; a synthetic organism, cell, cell line or strain; a recombinant virus or strain; a synthetic virus or strain; and the like.

In another aspect, provided herein is a method of determining the presence of a recombinant or synthetic organism, which may be a single cell, a multicellular organism or a virus, comprising a reference watermark that conveys a non-genetic message in a sample, said method comprising: sequencing nucleic acid material obtained from one or more organisms in said sample; transforming the nucleic acid sequence to a set of codon identifiers, wherein each codon identifier consists of three nucleotides of said sequence, and the transforming is performed in all three reading frames; determining a human readable symbol for each codon identifier in the sequence in all three reading frames, wherein said determination is based at least in part upon a symbol mapping that map codons identifiers corresponding to start codon(s) to human readable symbols that possess a disproportionally low frequency in the language of the watermark, and that maps codon identifiers corresponding to stop codon(s) to human readable symbols that possess a disproportionally high frequency in the language of the watermark; and comparing the human readable symbol sequence of all three reading frames to the reference watermark in said recombinant or synthetic organism, whereby the presence of the reference watermark in any reading frame of the nucleic acid material indicates the presence of the recombinant or synthetic organism in the sample.

Alternatively, provided herein is a method of determining the presence of a recombinant or synthetic organism, which may be a single cell, a multicellular organism or a virus, comprising a reference watermark that conveys a non-genetic message in a sample, said method comprising: sequencing nucleic acid material obtained from one or more organisms in said sample; transforming the nucleic acid sequence to a set of codon identifiers, wherein each codon identifier consists of three nucleotides of said sequence, and the transforming is performed in all three reading frames; determining a human readable symbol for each codon identifier in the sequence in all three reading frames, wherein said determination is based at least in part upon a symbol mapping that is configured to map a start codon to a human readable symbol with a frequency of distribution of less than one percent in the set of human readable symbols and is further configured to map a stop codon to a human readable symbol with a frequency of distribution of more than five percent in the set of human readable symbols; and comparing the human readable symbol sequence of all three reading frames to the reference watermark in said recombinant or synthetic organism, whereby the presence of the reference watermark in any reading frame of the nucleic acid material indicates the presence of the recombinant or synthetic organism in the sample.

A sample can be any sample that can contains a cell, multiple cells, a virus, or nucleic acid material from a cell, cells or virus, including without limitation, environmental samples, patient samples, veterinary samples, samples obtained from humans, animals, plants, viruses, bacteria, archaea, yeast, and any fractions or derivatives of any such samples. Samples can also be laboratory samples (e.g., for-profit and non-profit laboratories) and commercial samples.

In another aspect, provided herein is an apparatus for transforming a sequence of codon identifiers into a sequence of human readable symbols that conveys a non-genetic message, the apparatus comprising: a processor adapted to execute instructions; and a storage module, wherein the storage module comprises a data structure for mapping codon identifiers into human readable symbols, and a set of instructions which, when executed by the processor, generate a human readable symbol for each codon identifier read from a sequence of codon identifiers, wherein the human readable symbol generated is based at least in part upon the data structure; wherein the data structure is configured to map a start codon to a human readable symbol with a frequency of occurrence within a reference language that is less than a first predetermined threshold, and wherein the data structure is further configured to map a plurality of stop codons to human readable symbols with frequencies of occurrence within the reference language that are greater than a second predetermined threshold.

In another embodiment, the data structure maps a start codon to a human readable symbol with a frequency of distribution of less than one percent in the set of human readable symbols, and further maps a stop codon to a human readable symbol with a frequency of distribution of more than five percent in the set of human readable symbols.

In one preferred embodiment, the data structure does not map a codon identifier to a single letter representation of an amino acid residue normally assigned to that codon identifier in the standard genetic code. In another embodiment, the sequence of codon identifiers comprises at least one of an all-6 reading frame stop codon containing sequence 5' to a first codon identifier in the sequence, and/or an all-6 reading frame stop codon containing sequence 3' to the last codon identifier in the sequence.

In another aspect, provided herein is a computer-readable medium for use in a decoding machine, the computer-readable medium comprising instructions which, when executed by the decoding machine, perform a process comprising: identifying a sequence of codon identifiers in all three reading frames; and generating a human readable symbol for each codon identifier in the sequence; wherein the human readable symbol generated is based at least in part upon a mapping function configured to map a start codon to a human readable symbol that has a frequency of occurrence within a reference language that is smaller than every other human readable symbol of a first set of human readable symbols, and wherein the mapping function is further configured to map a stop codon to a human readable symbol that has a frequency of occurrence within the reference language that is larger than every other human readable symbol of the first set of human readable symbols.

Also provided herein is a computer-readable medium for use in a decoding machine, the computer-readable medium comprising instructions which, when executed by the decoding machine, perform a process comprising: identifying a sequence of codon identifiers in all three reading frames; and generating a human readable symbol for each codon identifier in the sequence of codon identifiers, wherein the human readable symbol generated is based upon a mapping function that maps codon identifiers corresponding to start codon(s) to human readable symbols that possess a disproportionally low frequency in the language of the watermark, and that maps codon identifiers corresponding to stop codon(s) to human readable symbols that possess a disproportionally high frequency in the language of the watermark (which conveys a non-genetic message).

In another aspect, provided herein is a method of transforming a first signal adapted to indicate a sequence of codon identifiers into a second signal adapted to indicate a sequence of human readable symbols that conveys a non-genetic message, the method comprising: receiving the first signal; determining a human readable symbol for each codon identifier in the sequence in all three reading frames, wherein said determining is based at least in part upon a mapping function configured to map a start codon to a first human readable symbol, wherein the first human readable symbol has a lower frequency of occurrence in a symbol sequence than one or more human readable symbols from a set of human readable symbols containing the first human readable symbol, and wherein the mapping function is further configured to map a stop codon to a second human readable symbol, wherein the second human readable symbol is contained within the set of human readable symbols, and wherein the second human readable symbol has a higher frequency of occurrence in the symbol sequence than one or more human readable symbols from the set of human readable symbols; and transforming the first signal into the second signal based upon the one or more determined human readable symbols.

Also provided herein is a method of transforming a first signal comprising a sequence of codon identifiers into a second signal to indicate a sequence of human readable symbols of a set of human readable symbols of a reference language that conveys a non-genetic message, the method comprising: identifying the first signal that indicates the sequence of codon identifiers; determining a human readable symbol for each codon identifier in the sequence in all three reading frames, wherein said determining a human readable symbol is based at least in part upon a mapping function that maps a start codon to a human readable symbol with a frequency of distribution of less than one percent in the set of human readable symbols, and further maps a stop codon to a human readable symbol with a frequency of distribution of more than five percent in the set of human readable symbols; and transforming the first signal into the second signal, wherein the second signal indicates the sequence of human readable symbols.

In another aspect, provided herein is an apparatus for converting a sequence of human readable symbols of a reference language that conveys a non-genetic message into a sequence of codon identifiers, the apparatus comprising: a processor configured to execute instructions; a memory module coupled to the processor and comprising instructions which, when executed by the processor, determine a codon identifier for each human readable symbol contained within the sequence of human readable symbols, wherein each codon identifier is determined upon reading a symbol map; and a data module coupled to the memory module, wherein the data module comprises the symbol map, wherein the symbol map is configured to map one or more start codons to respective human readable symbols that possess a disproportionally low frequency of occurrence in the reference language, and wherein the symbol map is further configured to map one or more stop codons to respective human readable symbols that possess a disproportionally high frequency in the reference language.

Also provided herein is an apparatus for converting a sequence of human readable symbols of a set of human readable symbols of a reference language that conveys a non-genetic message into a sequence of codon identifiers, the apparatus comprising: a processor that executes a sequence of instructions; a memory module coupled to the processor and comprising instructions for determining a codon identifier for each human readable symbol contained within the sequence of human readable symbols, wherein each codon identifier is determined upon reading a symbol map; and a data module coupled to the memory module, wherein the data module comprises the symbol map, the symbol map maps a human readable symbol with a frequency of distribution of less than one percent in the set of human readable symbols to a start codon, and the symbol map further maps a human readable symbol with a frequency of distribution of more than five percent in the set of human readable symbols to a stop codon.

In another aspect, provided herein is a computer-readable medium for use in an encoding machine, the computer-readable medium comprising instructions which, when executed by the encoding machine, perform a process comprising: receiving a sequence of human readable symbols that conveys a non-genetic message; and generating a codon identifier for each human readable symbol contained within the sequence, wherein the human readable symbol generated is based at least in part upon a mapping function configured to map a start codon to a first human readable symbol, wherein the first human readable symbol has a lower frequency of occurrence in a reference language than one or more human readable symbols from a set of human readable symbols containing the first human readable symbol, and wherein the mapping function is further configured to map a stop codon to a second human readable symbol, wherein the second human readable symbol is contained within the set of human readable symbols, and wherein the second human readable symbol has a higher frequency of occurrence in the reference language than one or more human readable symbols from the set of human readable symbols.

Also provided herein is a computer-readable medium for use in an encoding machine, the computer-readable medium comprising instructions which, when executed by the encoding machine, perform a process comprising: generating a codon identifier for each human readable symbol in a set of human readable symbols that conveys a non-genetic message, wherein the human readable symbol generated is based upon a mapping function that maps a human readable symbol with a frequency of distribution of less than one percent in the set of human readable symbols to a start codon, and that further maps a human readable symbol with a frequency of distribution of more than five percent in the set of human readable symbols to a stop codon.

In another aspect, provided herein is a method of generating a sequence of codon identifiers from a sequence of human readable symbols that conveys a non-genetic message, the method comprising: receiving the sequence of human readable symbols at a memory module; loading a symbol map within the memory module, wherein the symbol map is configured to determine a codon identifier that maps to each human readable symbol within the sequence, wherein the symbol map is further configured to map a human readable symbol with a frequency of occurrence that is less than a first predetermined threshold within a reference language to a start codon, and wherein the symbol map is further configured to map a human readable symbol with a frequency of occurrence that is greater than a second predetermined threshold within the reference language to a stop codon; and outputting a sequence of codon identifiers corresponding to each human readable symbol within the sequence.

Also provided herein is a method of generating a sequence of codon identifiers from a sequence of human readable symbols of a set of human readable symbols of a reference language that conveys a non-genetic message, the method comprising: identifying the sequence of human readable symbols at a memory module; and using a processor to read a symbol mapping for each human readable symbol in the sequence and determine a codon identifier which maps to the respective human readable symbol; wherein the symbol mapping maps a human readable symbol with a frequency of distribution of less than one percent in the set of human readable symbols to a start codon, and that further maps a human readable symbol with a frequency of distribution of more than five percent in the set of human readable symbols to a stop codon.

Various other aspects and embodiments will become more apparent with reference to the accompanying figures and detailed description provided below.

BRIEF DESCRIPTION OF THE DRAWINGS

FIG. 3 is a screen capture of an exemplary human readable symbol map which may be used to generate an encoded nucleic acid sequence with a low probability of biological impact.

FIG. 8A-8E provide exemplary codon tables based on the English language. FIG. 8A depicts an exemplary code in the "Alt" format; FIG. 8B depicts an exemplary code in the "Ctrl" format; FIG. 8C depicts an exemplary code in the "Default" format; FIG. 8D depicts an exemplary code in the "Shift" format; and FIG. 8E depicts an exemplary code.

DETAILED DESCRIPTION

Figure 1:
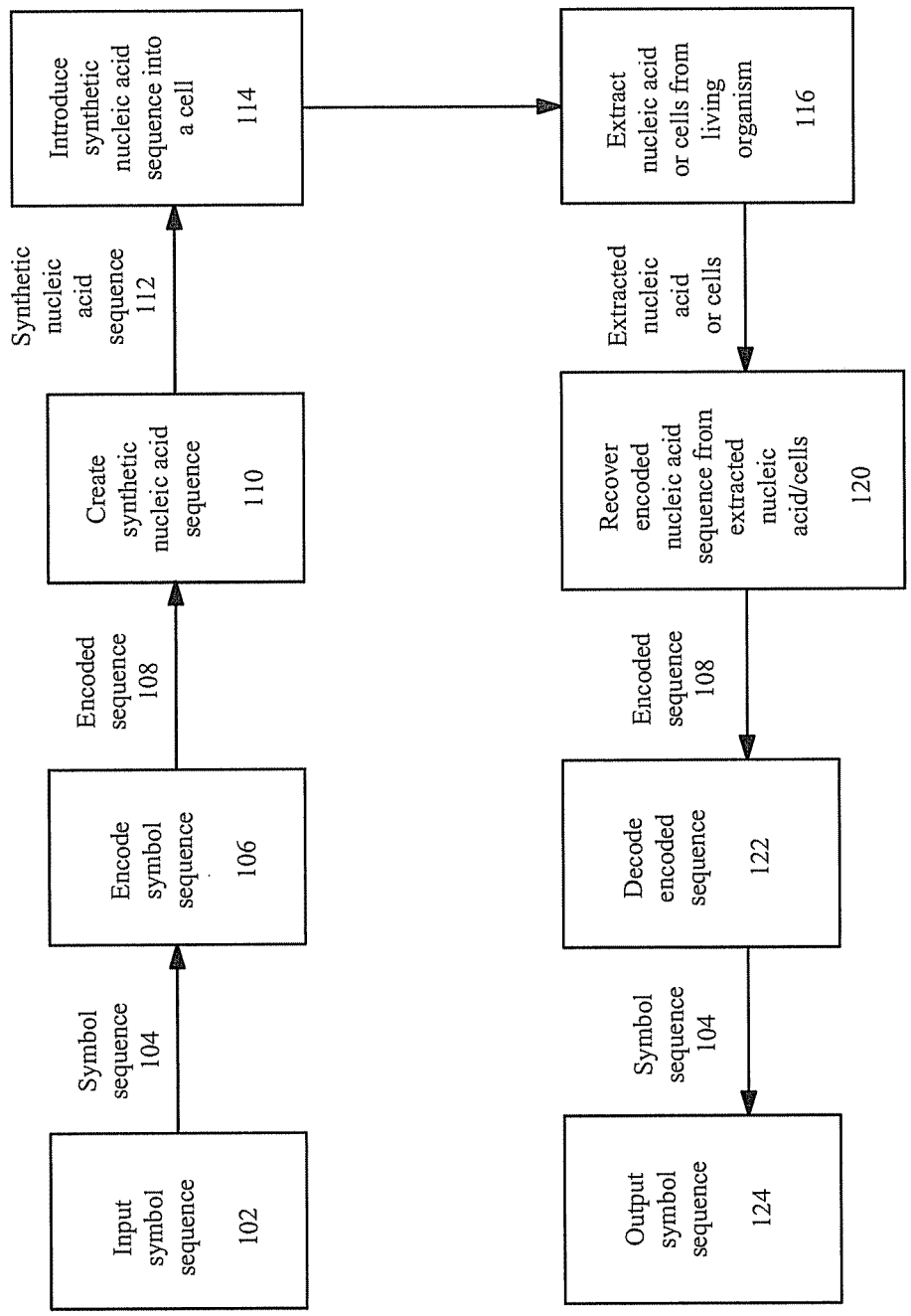
FIG. 1 is a functional sequence diagram illustrating an exemplary process of transcoding an input human readable symbol sequence and an encoded nucleic acid sequence.

The present application provides a system for encoding basic text into a synthetic nucleic acid sequence of codon identifiers and, furthermore, for decoding text therefrom.

Previous attempts to create such a system have utilized standard amino acid encoding codon tables, which results in unwanted biological effects from the nucleic acid encoded text. The present system described herein is specifically designed to ensure that the encoded text does not correspond to the codons used by or otherwise biologically active in a host organism. One embodiment encodes all letters in the American English alphabet, as well as all 10 numerals, mathematical symbols, typographical characters and common punctuation marks. The codon usage schemes described herein are designed for use in a variety of host organisms, and can be specifically tailored for optimization in a particular host. In the following description, reference is made to the accompanying figures in which it is shown by way of illustration specific embodiments can be practiced. It is to be understood that other embodiments can be used and structural changes can be made without departing from the scope of the present application. Elements of the embodiments described herein can be combined to make additional embodiments not specifically described that are also within the scope of the invention. Headings within the application are solely for the convenience of the reader, and do not limit in any way the scope of the invention or its embodiments.

All publications and patent applications mentioned in this specification are herein incorporated by reference to the same extent as if each individual publication or patent application was specifically and individually indicated to be incorporated by reference.

Unless defined otherwise, all technical and scientific terms used herein have the same meaning as commonly understood by one of ordinary skill in the art to which this invention is related. The following terms are defined for purposes of the invention as described herein.

As used herein, the terms "application", "computer program", "program", and "software" include without limitation any sequence of human or machine recognizable steps that are adapted to be processed by a computer. Such may be rendered in any programming language or environment including, without limitation, C/C++, Fortran, COBOL, PASCAL, Perl, Prolog, Python, MATLAB, assembly language, scripting languages, markup languages (e.g., HTML, SGML, XML, VoXML), functional languages (e.g., APL, Erlang, Haskell, Lisp, ML, F# and Scheme), as well as object-oriented environments such as the Common Object Request Broker Architecture (CORBA) and Java™ (including J2ME, Java Beans, etc.).

As used herein, the term "display" includes any type of device or medium adapted to display information, including without limitation cathode ray tube displays (CRTs), liquid crystal displays (LCDs), thin film transistor displays (TFTs), digital light processor displays (DLPs), plasma displays, light emitting diodes (LEDs) or diode arrays, incandescent devices, and fluorescent devices. Display devices also include less dynamic devices such as printers, e-ink devices, and other similar structures.

As used herein, the terms "local" and "remote" refer generally to devices, entities, or users that are serviced by separate sets of processes. These terms are intended to be relative, and bear no absolute reference or connotation to the physical location of the executed processes of the served device, entities, or users.

As used herein, the term "memory" includes any type of integrated circuit or other storage device adapted for storing digital data including, without limitation, ROM, PROM, EEPROM, DRAM, SDRAM, DDR/2 SDRAM, EDO/FPMS, RLDRAM, SRAM, "flash" memory (e.g., NAND/NOR), and PSRAM.

As used herein, the term "module" refers to any type of software, firmware, hardware, or combination thereof that is designed to perform a desired function.

As used herein, the terms "processor," "microprocessor," and "digital processor" include all types of digital processing devices including, without limitation, digital signal processors (DSPs), reduced instruction set computers (RISC), general-purpose (CISC) processors, microprocessors, gate arrays (e.g., FPGAs), programmable logic devices (PLDs), reconfigurable compute fabrics (RCFs), array processors, and application-specific integrated circuits (ASICs). Such processors may be contained on a single unitary IC die or distributed across multiple components.

As used herein in the context of introducing nucleic acids into cells or organisms, the terms "introducing", "transfection", "transformation", or "transduction", refer to the introduction of one or more exogenous nucleic acid sequences or polynucleotides into a host cell or organism by using one or more physical or chemical methods as are known in the art. Many transfection techniques are known to those of ordinary skill in the art including, but not limited to, calcium phosphate DNA co-precipitation (see Methods in Molecular Biology, Vol. 7, Gene Transfer and Expression Protocols, Ed. E. J. Murray, Humana Press (1991)); DEAE-dextran; electroporation; cationic liposome-mediated transfection; tungsten particle-facilitated microparticle bombardment (Johnston, S. A., *Nature* 346: 776-777 (1990)); and strontium phosphate DNA co-precipitation (Brash D. E. et al., *Molec. Cell. Biol.* 7: 2031-2034 (1987)).

As used herein in the general context of transforming a sequence, set or signal (such as a sequence of nucleic acid residues or codon identifiers), the term "transform" refers simply to changing or converting a first sequence, set, or signal into a second sequence, set, or signal.

As used herein, "DNA isolation or extraction" refers to any procedure used to collect DNA from a sample for subsequent analysis. For example, there are three basic steps and one optional step in a DNA extraction: (i) breaking the cells open, typically referred to as cell disruption or cell lysis, to expose the DNA within (commonly achieved by physically grinding or sonicating the sample, or chemically treating the sample); (ii) removing membrane lipids by adding a detergent; (iii) removing proteins by adding a protease (optional); and (iv) precipitating the DNA with an alcohol (usually ice-cold ethanol or isopropanol). Since DNA is insoluble in these alcohols, it will aggregate together, resulting in a pellet upon centrifugation; this step also removes alcohol-soluble salt. Refinements of the technique include adding a chelating agent to sequester divalent cations such as $Mg^{2+}$ and $Ca^{2+}$; this stops DNase enzymes from degrading the DNA. Cellular and histone proteins bound to the DNA can be removed either by adding a protease or by having precipitated the proteins with sodium or ammonium acetate, or extracted them with a phenol-chloroform mixture prior to the DNA-precipitation. If desired, the DNA can be redissolved in a slightly alkaline buffer or in ultra-pure water.

As used herein, "RNA isolation or extraction" refers to any procedure used to collect RNA from a sample for subsequent analysis. Several methods can be used to isolate RNA from samples; the most common of these is guanidinium thiocyanate-phenol-chloroform extraction.

As used herein, the term "DNA sequencing" refers to any sequencing method for determining the order of the nucleotide bases (adenine, guanine, cytosine, and thymine) in a molecule of DNA. Methods include, but are not limited to, Maxam-Gilbert sequencing, chain termination methods, dye-terminator sequencing, automated DNA-sequencing, in vitro cloning amplification, parallelized sequencing by synthesis, sequencing by ligation, microfluidic Sanger sequencing and sequencing by hybridization.

As used herein, "oligonucleotide synthesis" refers to the chemical synthesis of relatively short fragments of nucleic acids or codon identifiers with defined chemical structure (sequence). The technique is useful in because it provides a rapid and inexpensive access to custom-made oligonucleotides of a desired sequence. Whereas enzymes synthesize DNA and RNA in a 5' to 3' direction, chemical oligonucleotide synthesis is carried out in the opposite, 3' to 5' direction. Currently, the process is implemented as solid-phase synthesis using phosphoramidite method and A, C, G, T (2'-deoxy only), and U (ribo only) nucleoside phosphoramidites or 2'-deoxynucleoside phosphoramidites as building blocks. To obtain the desired oligonucleotide, the building blocks are sequentially coupled to the growing oligonucleotide chain in the order required by the sequence of the product.

As used herein, "nucleic acid synthesis" refers to the process of synthesizing an artificially designed sequence (e.g., a gene or a nucleic acid sequence which may contain a watermark) into a physical nucleic acid sequence.

The terms "cells", "cell cultures", "cell line", "recombinant host cells", "recipient cells" and "host cells" are often used interchangeably and will be clear from the context in which they are used. These terms include the primary subject cells and any progeny thereof, without regard to the number of transfers. It should be understood that not all progeny are exactly identical to the parental cell (due to deliberate or inadvertent mutations or differences in environment); however, such altered progeny are included in these terms, so long as the progeny retain the same functionality as that of the originally transformed cell. For example, though not limited to, such a characteristic might be the ability to include a non-genetic message, such as a watermark. The cell line can be any of those known in the art or described herein. A "clone" is a population of cells derived from a single cell or common ancestor by mitosis.

As used herein, the term "nucleotide" refers to a monomeric unit of a polynucleotide that consists of a heterocyclic base, a sugar, and one or more phosphate groups. The naturally occurring bases, (guanine, (G), adenine, (A), cytosine, (C), thymine, (T), and uracil (U)) are derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleic acids are linked via phosphate bonds to form nucleic acids, or polynucleotides, though many other linkages are known in the art (such as, though not limited to phosphorothioates, boranophosphates and the like).

As used herein, the terms "nucleic acid", "nucleotide" and "polynucleotide" refer to a polymeric form of nucleotides of any length, either ribonucleotides (RNA) or deoxyribonucleotides (DNA). These terms refer to the primary structure of the molecules and, thus, include double- and single-stranded DNA, and double- and single-stranded RNA. These terms include, as equivalents, natural or synthetic nucleic acids, analogs of either RNA or DNA made from nucleotide analogs and modified polynucleotides such as, though not limited to, methylated and/or capped polynucleotides. Nucleic acid sequences can be referred to as having a 5' end and a 3' end as is known in the art, which can be used as reference points for other sequences, for example, as being the 5' (also upsteam) or 3' (also downstream) to a codon identifier in a sequence.

As used herein, a "DNA molecule" refers to the polymeric form of deoxyribonucleotides (adenine, guanine, thymine, and cytosine) in its either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA). An "RNA molecule" refers to the polymeric form of ribonucleotides (adenine, guanine, uracil, and cytosine), which is typically, but not always, single-stranded.

Although embodiments may be described and illustrated in terms of deoxyribonucleic acid (DNA) sequences and corresponding nucleotide bases, it should be understood that the embodiments are not so limited, but are additionally applicable to other types of nucleic acids and nucleotide bases (including, for example, ribonucleic acid (RNA), such as messenger ribonucleic acid (mRNA)). Furthermore, although embodiments may be described and illustrated herein in terms of a single transcoder configured to both encode and decode an input human readable symbol sequence, it should be understood that the associated encoding and decoding logic may be separated and/or distributed among multiple systems, devices, and/or computer networks.

As used herein, a nucleic acid "coding sequence" or "coding region" is a region of a nucleic acid sequence which can be transcribed and/or translated into a polypeptide when placed under the control of appropriate expression control sequences and in the presence of appropriate cellular machinery or enzymes. In other words, a coding sequence provides one type of genetic message to the cell containing the sequence. The boundaries of the coding sequence (the "open reading frame" or "ORF") are determined by a start codon at the 5' terminus (encoding the amino terminus of a peptide or polypeptide) and a translation stop codon at the 3' terminus (encoding the carboxyl terminus of a peptide or polypeptide). For example, in most instances ATG and AUG denote sequences of DNA and RNA respectively that are the start codon or initiation codon encoding the amino acid methionine (Met) in eukaryotes and a modified Met (fMet) in prokaryotes, although alternate start codons, mainly GUG and UUG, may be used in prokaryotes. In the standard genetic code, there are three stop codons: UAG (in RNA)/TAG (in DNA) ("amber"), UAA/TAA ("ochre"), and UGA/TGA ("opal" or "umber"); although several variations to this most common set are known. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence is, usually, located 3' to the coding sequence. As used herein, the term "non-coding sequence" or "non-coding region" refers to regions of a nucleic acid sequence that are not transcribed and/or translated into amino acids (e.g., un-translated regions, signal sequences, etc.).

As used herein term "reading frame" refers to one of the six possible reading frames, three in each direction (5' and 3'), of the nucleic acid molecule. The reading frame that is used determines which codons are used to encode amino acids within the coding sequence of a DNA molecule. When decoding sequences in methods and apparatus described herein, all three reading frames in the 5' direction are typically used to ensure detection of any non-genetic message encoded in a nucleic acid sequence. As used herein, an all-six or all-6 reading frame stop codon containing sequence refers to a sequence that will mandatorily cause termination of transcription and translation proceeding in either the 5' or 3' direction, in any of the three respective reading frames (e.g., TTAACTAGCTAA; SEQ ID NO: 1).

Using the exemplary sequence the three 5' reading frames would be:

TTA ACT AGC TAA (SEQ ID NO: 1), with the stop codon in the fourth triplet;

TAA CTA GCT AA- (SEQ ID NO: 2), with the stop codon in the first triplet; and

AAC TAG CTA A-- (SEQ ID NO: 3), with the stop codon in the second triplet.

Using the same exemplary sequence the three 3' reading frames (anti-sense or complementary strand) would be:

TTA GCT AGT TAA (SEQ ID NO: 4), with the stop codon in the fourth triplet;

TAG CTA GTT AA- (SEQ ID NO: 5), with the stop codon in the first triplet; and

ACG TAG TTA A-- (SEQ ID NO: 6), with the stop codon in the second triplet.

As used herein, an "antisense" nucleic acid molecule comprises a nucleic acid sequence which is complementary to a "sense" nucleic acid encoding a protein, e.g., complementary to the coding strand of a double-stranded DNA molecule, complementary to an mRNA sequence or complementary to the coding strand of a gene. Accordingly, an antisense nucleic acid molecule can be hydrogen-bonded to a sense nucleic acid molecule.

As used herein, a "codon" refers to the three nucleotides which, when transcribed and translated, encode a single amino acid residue; or in the case of UUA, UGA or UAG encode a termination signal. As used herein, a "wobble position" refers to the third position of a codon. Codons of the standard genetic code encoding amino acids are well known in the art and are provided for convenience herein in Table 1.

TABLE 1

Codon Table

| Amino Acid | Amino Acid Abbr. | Codon |
| --- | --- | --- |
| Alanine | A | GCA |
|  | A | GCC |
|  | A | GCG |
|  | A | GCU |
| Cysteine | C | UGC |
|  | C | UGU |
| Aspartate | D | GAC |
|  | D | GAU |
| Glutamate | E | GAA |
|  | E | GAG |
| Phenylalanine | F | UUC |
|  | F | UUU |
| Glycine | G | GGA |
|  | G | GGC |
|  | G | GGG |
|  | G | GGU |
| Histidine | H | CAC |
|  | H | CAU |
| Isoleucine | I | AUA |
|  | I | AUC |
|  | I | AUU |
| Lysine | K | AAA |
|  | K | AAG |
| Leucine | L | CUA |
|  | L | CUC |
|  | L | CUG |
|  | L | CUU |
|  | L | UUA |
|  | L | UUG |
| Methionine | M | AUG |
| Asparagine | N | AAC |
|  | N | AAU |
| Proline | P | CCA |
|  | P | CCC |
|  | P | CCG |
|  | P | CCU |
| Glutamine | Q | CAA |
|  | Q | CAG |
| Arginine | R | AGA |
|  | R | AGG |
|  | R | CGA |
|  | R | CGC |
|  | R | CGG |
|  | R | CGU |
| Serine | S | AGC |
|  | S | AGU |
|  | S | UCA |
|  | S | UCC |
|  | S | UCG |
|  | S | UCU |

TABLE 1-continued

Codon Table

| Amino Acid | Amino Acid Abbr. | Codon |
|---|---|---|
| Threonine | T | ACA |
|  | T | ACC |
|  | T | ACG |
|  | T | ACU |
| Valine | V | GUA |
|  | V | GUC |
|  | V | GUG |
|  | V | GUU |
| Tryptophan | W | UGA |
|  | W | UGG |
| Tyrosine | Y | UAC |
|  | Y | UAU |
| STOP | STOP | UAA |
| STOP | STOP | UAG |

Abbr: abbreviation. It should be understood that the codons specified above are for RNA sequences. The corresponding codons for DNA have a T substituted for U. Each codon corresponds to an amino acid which can be abbreviated into a single letter of the alphabet. In preferred embodiments, three nucleotide codon identifiers do not correspond to these same single letters in the symbol mapping, such that any natural language information encoded as codon identifiers is extremely unlikely to correspond to a nucleic acid sequence with biological function. As such, the encoded sequence is unlikely to be lethal to a cell or organism comprising the sequence, or subject to genetic selection in a cellular context, or to correspond to a sequence that would come into existence naturally.

Optimal codon usage is indicated by codon usage frequencies for expressed genes, for example, as shown in the codon usage chart from the program "Human-High.cod" from the Wisconsin Sequence Analysis Package, Version 8.1, Genetics Computer Group, Madison, Wis. Codon usage is also described in, for example, R. Nussinov, "Eukaryotic Dinucleotide Preference Rules and Their Implications for Degenerate Codon Usage," *J. Mol. Biol.* 149: 125-131 (1981). The codons which are most frequently used in highly expressed human genes are presumptively the optimal codons for expression in human host cells and, thus, form the bases for constructing a synthetic coding sequence. In alternate species, codon usage may vary (also known as codon biase), and sequences may be codon optimized to reflect such differences for use of sequences in different organisms. A useful source of information can be found on the internet at the www URL kazusa.or.jp/codon/, in a Codon Usage Database.

As used herein, a "codon identifier" refers to nucleotides that code for a single human readable symbol of a reference language, preferably a triplet or three nucleotides. A set or sequence of codon identifiers preferably do not correspond to the sequence of a naturally-occurring gene or other biologically active sequence. Rather, the one or more codon identifiers correspond to one or more letters, one or more numbers, one or more spaces, one or more punctuation marks (e.g., " , . ; [ ] { } ( ) : ! ? and '), one or more mathematical symbols (#, (, ), ?, *, +, =, $, %, etc.), one or more typographical characters (e.g., @, ©, ™, ®, §, etc.), one or more new lines, or a combination of any thereof and are made up of three nucleotides. Exemplary codon identifiers are provided in more detail below and in the accompanying figures. When combined into a synthetic nucleic acid sequence, a series of codon identifiers conveys a non-genetic message.

The following Table 2 illustrates exemplary human readable symbols recognizable in the English language. Any other characters or symbols could readily be incorporated as desired by the user.

TABLE 2

Exemplary human readable symbols

| Punctuation mark examples | " | " | " | , | : | [ | { | ( | ! |
|  | ' | ' | ' | . | ; | ] | } | ) | ? |
| Mathematical symbol examples | # | + | * | % | < | \| | ± | « | ≤ |
|  | Σ | − | / | = | > | ~ | _ | » | ≥ |
| Typographical character examples | @ | © | ™ | ® | § | / | \ | ^ | ☺ |
|  | ¶ | ... | † | · | → | ↔ | ‡ | ∞ | $ |

As used herein, a "watermark" may include, but is not limited to, a copyright notice, a trademark, a company identifier, a name, a phrase, a sentence, a quotation, genetic information, unique identifying information, data, or a combination of any thereof. Watermarks can contain letters, numbers, symbols, punctuation, or any other definable human readable symbol. As used herein, "data" includes, for example, DNA-based computations including use of DNA as a processor. Encoded messages or watermarks may be technical or otherwise meaningful (such as various identifiers), or may be fanciful or arbitrary (such as literary quotations). The encoded message or watermark conveys a "non-genetic message", for example, it is not transcribed or translated, it cannot bind or be bound, transport or be transported by traditional cellular processes, and it is otherwise biologically silent or inocuous in the cell within which it is present. The size of a watermark is based on the size of a cell/organism. Sequences containing messages or watermarks can have lengths up to about 40 Kb, up to about 35 Kb, up to about 30 Kb, up to about 25 Kb, up to about 20 Kb, up to about 15 Kb, up to about 10 Kb, up to about 5 Kb, up to about 3 Kb, up to about 2 Kb, up to about 1 Kb, up to about 0.5 Kb, up to about 0.1 Kb, or any value therebetween. The length of the sequence generally does not exceed the length of a gene, genome, plasmid, or chromosome into which it is inserted. Insertion can be placement within a gene, genome, plasmid, or chromosome, or replacement of all or a portion thereof.

As used herein, a "reference language" refers to any language on the planet including, but not limited to, Afrikaans, Albanian, Arabic, Aranese (Occitan), Armenian, Basque, Cantonese Chinese, Catalan, Chipewyan, Cree, Croatian, Cyrillic, Czech, Danish, Dutch, English, Faroese, Farsi, Finish, French, German, Galician, Gwich'in, Greek, Hebrew, Hindi, Hungarian, Korean, Icelandic, Inuinnaqtun, Inuktitut, Inuvialuktun, Italian, Japanese, Kalaallisut, Mandarin, Mazandarani, Norwegian, Persian, Polish, Portuguese, Punjabi, Romanian, Russian, Rusyn, Sami, Sanskrit, North and South Slavey, Slovene, Spanish, Swahili, Swedish, Tahitian, Tibetan, Tswana, Turkish, Ukranian, Urdu, Uyghur, Uzbek, Venda, Vietnamese, Welch, Xhosa, Yiddish, Zhuang, and Zulu.

As used herein, "isolated" (used interchangeably with "substantially pure") in the context of an isolated biomolecule such as an isolated protein or nucleic acid, is a biomolecule removed from the context in which the biomolecule exists in nature. For example, an isolated protein or nucleic acid molecule is removed from the cell or organism with which it is associated in its natural state. An isolated biomolecule can be, in some instances, partially or substantially purified, for example, an isolated nucleic acid molecule can be a nucleic acid sequence that has been excised from the chromosome, genome, or episome that it is integrated into in nature.

Encoder

Provided herein are means for encoding a sequence of human readable symbols of a reference language that conveys a non-genetic message into one or more codon identifiers. Such means include, for example, an apparatus, systems, and a computer-readable medium for generating a sequence of codon identifiers from a reference language.

Provided herein is an apparatus for converting a sequence of human readable symbols of a reference language that conveys a non-genetic message into a sequence of codon identifiers, the apparatus comprising: a processor configured to execute instructions; a memory module coupled to the processor and comprising instructions which, when executed by the processor, determine a codon identifier for each human readable symbol contained within the sequence of human readable symbols, wherein each codon identifier is determined upon reading a symbol map; and a data module coupled to the memory module, wherein the data module comprises the symbol map, wherein the symbol map is configured to map one or more start codons to respective human readable symbols that possess a disproportionally low frequency of occurrence in the reference language, and wherein the symbol map is further configured to map one or more stop codons to respective human readable symbols that possess a disproportionally high frequency in the reference language.

The goal is to generate a nucleic acid sequence that is not genetically viable, and thus does not have a biological impact on a recombinant or synthetic cell, or on a recombinant or synthetic virus, comprising the sequence. To that end, the nucleic acid sequence should contain frequent occurrences of stop codons, and few occurrences of start codons. As an example, a start codon may be mapped to a character in the English language that is rarely used, such as *, such that a start codon would rarely be mapped into the synthetic nucleic acid sequence; the reverse complement of the start codon can be assigned to the rare "Y"; and a stop codon may be mapped to a character in the English language that is most commonly used, such as the letter E, A or T, such that a stop codon would be frequently be mapped into the synthetic nucleic acid sequence. The reverse complement of two of the stop codons are the common characters "R" and "H". These measure ensure that a watermark can be transcribed in either direction and any potential open reading frame will be short in the +0 and −0 reading frames. The code can be designed such that common two-character combinations such as "CH" ensure that the −1, −2, +1 and +2 reading frames do not tend to avoid stop codons. Common and uncommon characters can be distributed evenly across the chart to help guard against low-complexity sequences being added by patterns into a watermark text. A disproportionally low frequence of occurrence in the reference language typically refers to a symbol that has a frequency of distribution of less than one percent in the set of human readable symbols. A disproportionally high frequence of occurrence in the reference language typically refers to a symbol that has a frequency of distribution of more than five percent in the set of human readable symbols. For example, in the symbol map shown in FIG. 3, the character * would have disproportionally low frequence of occurrence in conventional text patterns in the English language, and the alphabetical characters E, A and T would have a disproportionally high frequence of occurrence in conventional text patterns in the English language.

Provided herein is an apparatus for converting a sequence of human readable symbols of a set of human readable symbols of a reference language that conveys a non-genetic message into a sequence of codon identifiers, the apparatus comprising: a processor that executes a sequence of instructions; a memory module coupled to the processor and comprising instructions for determining a codon identifier for each human readable symbol contained within the sequence of human readable symbols, wherein each codon identifier is determined upon reading a symbol map; and a data module coupled to the memory module, wherein the data module comprises the symbol map, the symbol map maps a human readable symbol with a frequency of distribution of less than one percent in the set of human readable symbols to a start codon, and the symbol map further maps a human readable symbol with a frequency of distribution of more than five percent in the set of human readable symbols to a stop codon.

Provided herein is a computer-readable medium for use in an encoding machine, the computer-readable medium comprising instructions which, when executed by the encoding machine, perform a process comprising: receiving a sequence of human readable symbols that conveys a non-genetic message; and generating a codon identifier for each human readable symbol contained within the sequence, wherein the human readable symbol generated is based at least in part upon a mapping function configured to map a start codon to a first human readable symbol, wherein the first human readable symbol has a lower frequency of occurrence in a reference language than one or more human readable symbols from a set of human readable symbols containing the first human readable symbol, and wherein the mapping function is further configured to map a stop codon to a second human readable symbol, wherein the second human readable symbol is contained within the set of human readable symbols, and wherein the second human readable symbol has a higher frequency of occurrence in the reference language than one or more human readable symbols from the set of human readable symbols.

Provided herein is a computer-readable medium for use in an encoding machine, the computer-readable medium comprising instructions which, when executed by the encoding machine, perform a process comprising: generating a codon identifier for each human readable symbol in a set of human readable symbols that conveys a non-genetic message, wherein the human readable symbol generated is based upon a mapping function that maps a human readable symbol with a frequency of distribution of less than one percent in the set of human readable symbols to a start codon, and that further maps a human readable symbol with a frequency of distribution of more than five percent in the set of human readable symbols to a stop codon.

Provided herein is a method of generating a sequence of codon identifiers from a sequence of human readable symbols, the method comprising: receiving the sequence of human readable symbols that conveys a non-genetic message at a memory module; loading a symbol map within the memory module, wherein the symbol map is configured to determine a codon identifier that maps to each human readable symbol within the sequence, wherein the symbol map is further configured to map a human readable symbol with a frequency of occurrence that is less than a first predetermined threshold within a reference language to a start codon, and wherein the symbol map is further configured to map a human readable symbol with a frequency of occurrence that is greater than a second predetermined threshold within the reference language to a stop codon; and outputting a sequence of codon identifiers corresponding to each human readable symbol within the sequence.

Provided herein is a method of generating a sequence of codon identifiers from a sequence of human readable symbols of a set of human readable symbols of a reference language that conveys a non-genetic message, the method comprising: identifying the sequence of human readable symbols at a memory module; and using a processor to read a symbol mapping for each human readable symbol in the sequence and determine a codon identifier which maps to the respective human readable symbol; wherein the symbol mapping maps a human readable symbol with a frequency of distribution of less than one percent in the set of human readable symbols to a start codon, and that further maps a human readable symbol with a frequency of distribution of more than five percent in the set of human readable symbols to a stop codon.

Decoder

Provided herein are means for decoding a sequence of one or more codon identifiers into one or more human readable symbols of a reference language that conveys a non-genetic message. Such means include, for example, an apparatus, systems, and a computer-readable medium. When decoding a nucleic acid sequence comprising of one or more codon identifiers, it will initially be unknown from the source sequence which 5' reading frame may contain the non-genetic message or watermark, and therefore, all three 5' reading frames must be analyzed.

Provided herein is an apparatus for transforming a sequence of codon identifiers into a sequence of human readable symbols that conveys a non-genetic message, the apparatus comprising: a processor adapted to execute instructions; and a storage module, wherein the storage module comprises a data structure for mapping codon identifiers into human readable symbols, and a set of instructions which, when executed by the processor, generate a human readable symbol for each codon identifier read from a sequence of codon identifiers, wherein the human readable symbol generated is based at least in part upon the data structure; wherein the data structure is configured to map a start codon to a human readable symbol with a frequency of occurrence within a reference language that is less than a first predetermined threshold, and wherein the data structure is further configured to map a plurality of stop codons to human readable symbols with frequencies of occurrence within the reference language that are greater than a second predetermined threshold.

In another embodiment, the data structure maps a start codon to a human readable symbol with a frequency of distribution of less than one percent in the set of human readable symbols, and further maps a stop codon to a human readable symbol with a frequency of distribution of more than five percent in the set of human readable symbols.

In one embodiment, the data structure does not map a codon identifier to a single letter representation of an amino acid residue normally assigned to that codon identifier in the standard genetic code.

In another embodiment, the sequence of codon identifiers comprises at least one of an all-6 reading frame stop codon containing sequence 5' to a first codon identifier in the sequence, and an all-6 reading frame stop codon containing sequence 3' to the last codon identifier in the sequence.

Provided herein is a computer-readable medium for use in a decoding machine, the computer-readable medium comprising instructions which, when executed by the decoding machine, perform a process comprising: identifying a sequence of codon identifiers; and generating a human readable symbol for each codon identifier in the sequence; wherein the human readable symbol generated is based at least in part upon a mapping function configured to map a start codon to a human readable symbol that has a frequency of occurrence within a reference language that is smaller than every other human readable symbol of a first set of human readable symbols, and wherein the mapping function is further configured to map a stop codon to a human readable symbol that has a frequency of occurrence within the reference language that is larger than every other human readable symbol of the first set of human readable symbols.

Provided herein is a computer-readable medium for use in a decoding machine, the computer-readable medium comprising instructions which, when executed by the decoding machine, perform a process comprising: identifying a sequence of codon identifiers; and generating a human readable symbol for each codon identifier in the sequence of codon identifiers, wherein the human readable symbol generated is based upon a mapping function that maps codon identifiers corresponding to start codon(s) to human readable symbols that possess a disproportionally low frequency in the language of the watermark, and that maps codon identifiers corresponding to stop codon(s) to human readable symbols that possess a disproportionally high frequency in the language of the watermark.

In one embodiment, the mapping function does not map a codon identifier to a single letter representation of an amino acid residue normally assigned to that codon identifier in the standard genetic code.

In another embodiment, the sequence of codon identifiers comprises at least one of an all-6 reading frame stop codon containing sequence 5' to a first codon identifier in the sequence, and an all-6 reading frame stop codon containing sequence 3' to the last codon identifier in the sequence.

Provided herein is a method of transforming a first signal adapted to indicate a sequence of codon identifiers into a second signal adapted to indicate a sequence of human readable symbols that conveys a non-genetic message, the method comprising: receiving the first signal; determining a human readable symbol for each codon identifier in the sequence, wherein said determining is based at least in part upon a mapping function configured to map a start codon to a first human readable symbol, wherein the first human readable symbol has a lower frequency of occurrence in a human readable symbol sequence than one or more human readable symbols from a set of human readable symbols containing the first human readable symbol, and wherein the mapping function is further configured to map a stop codon to a second human readable symbol, wherein the second human readable symbol is contained within the set of human readable symbols, and wherein the second human readable symbol has a higher frequency of occurrence in the human readable symbol sequence than one or more symbols from the set of human readable symbols; and transforming the first signal into the second signal based upon the one or more determined human readable symbols.

Provided herein is a method of transforming a first signal comprising a sequence of codon identifiers into a second signal to indicate a sequence of human readable symbols of a set of human readable symbols of a reference language that conveys a non-genetic message, the method comprising: identifying the first signal that indicates the sequence of codon identifiers; determining a human readable symbol for each codon identifier in the sequence, wherein said determining a human readable symbol is based at least in part upon a mapping function that maps a start codon to a human readable symbol with a frequency of distribution of less than one percent in the set of human readable symbols, and further maps a stop codon to a human readable symbol with a frequency of distribution of more than five percent in the set of human readable symbols; and transforming the first signal into the second signal, wherein the second signal indicates the sequence of human readable symbols.

In one embodiment, the mapping function does not map a codon identifier to a single letter representation of an amino acid residue normally assigned to that codon identifier in the standard genetic code.

In another embodiment, the sequence of codon identifiers comprises at least one of an all-6 reading frame stop codon containing sequence 5' to a first codon identifier in the sequence, and an all-6 reading frame stop codon containing sequence 3' to the last codon identifier in the sequence.

Exemplary Embodiments of Encoding and Decoding

FIG. 1 is a functional sequence diagram illustrating an exemplary high-level process of translating an input symbol sequence into an encoded nucleic acid sequence that can be stored within any genetic material of an organism, such as that contained in a chromosome or genome in one or more cells of a sample, living organism and the like. The genetic material (e.g., DNA) of the cell/organism can be subsequently harvested or extracted using standard techniques which are well known in the art, so that the encoded nucleotide sequence can later be determined. The encoded nucleotide sequence may then be parsed and decoded in order to generate the original symbol sequence. Although the following description provides computer-assisted encoding and/or decoding processes, any of the methods described herein may be performed manually.

At block 102, a symbol sequence 104 is provided. The symbol sequence 104 may comprise any number of discrete representations or symbols, including alphanumeric and non-standard symbols, ASCII or ANSI symbols, control symbols, and/or other types of metadata.

A wide variety of possible symbol sequences 104 may be utilized. For example, a symbol sequence 104 may include the names of people or organizations, trademarks and/or copyright notices, serial numbers, text messages, times and/or dates, tags and other indicators, classified information, data, digital computer instructions, graphics, video, information intended to be operated upon by a DNA based computer, etc. Myriad other types of content may also be contained within a symbol sequence 104 and are contemplated herein.

The symbol sequence 104 may also be provided in any number of ways. In some embodiments, for example, the symbol sequence 104 may be provided by a connected keyboard, touchpad, mouse, microphone, or other input peripheral. In other embodiments, the symbol sequence 104 may be read from one or more files or data streams. These files or data streams may be accessed on a local system (for example, on a local hard disk or other non-volatile memory source), a remote system (for example, on a networked system or server accessible over the Internet), or a removable media device (for example, a floppy disk, external hard drive, flash drive, smart card, or other serial bus device).

At block 106, an encoded sequence 108 of nucleotides is generated based upon the provided symbol sequence 104. A symbol map 220 (for example, as that shown in FIG. 3) may be used to translate each symbol in the symbol sequence 106 into a sequence known as a codon identifier, preferably a tri-nucleotide. In some embodiments, the symbol map 220 may be stored locally (for example, within a lookup table, database, or other reference structure resident within a local memory module). In other embodiments, the symbol map 220 may be stored within the memory of one or more remote systems.

At block 110, a synthetic nucleic acid sequence 112 may then be created from the encoded sequence 108 specified. Conventional techniques in molecular biology and DNA synthesis may be used, for example, to create a synthetic nucleic acid sequence 112 which contains the same codon identifier ordering as the encoded sequence 108.

At block 114, the synthetic nucleic acid sequence 112 may then be introduced into a cell or living organism using standard techniques. The synthetic nucleic acid sequence 112 may be directly or indirectly introduced into the organism. Once the synthetic nucleic acid sequence 112 is introduced into the cell or organism, cells can then harbor the synthetic nucleic acid sequence 112, effectively serving as a memory source for the encoded sequence 108.

In order to recover the symbol sequence 104 from the cell or organism (e.g., a virus or a multicellular organism), nucleic acid can be or cells can be extracted (as shown at block 116). Note that a variety of conventional extraction techniques may be used to extract the genetic material from a recombinant cell, a synthetic cell, or a recombinant or synthetic organism. The extracted cells 118 may then be analyzed at block 120 in order to recover the originally encoded sequence 108.

Once the encoded sequence 108 has been recovered, this sequence 108 may then be parsed and decoded at block 122. A symbol map 220 (for example, as that shown in FIG. 3) may be used to decode/translate each codon identifier 302 into a corresponding symbol 304 of the original symbol sequence 106. In this manner, all human readable symbols from the original symbol sequence 106 may be reproduced.

The symbol sequence 106 may then be output at block 124 in any number of ways. In some embodiments, for example, the symbol sequence 104 may be output directly on one or more output devices. Any device capable of writing or displaying data may be used for such purposes, including, for example, display devices (e.g., monitors), printers, projectors, televisions, speakers, networked devices (e.g., computers, digital cameras, personal data assistants, memory devices, etc.) and/or other output peripherals. In some embodiments, the symbol sequence 104 is configured to be written to one or more files that may be stored within a local memory source. In yet other embodiments, the symbol sequence 104 may be output by human writing on implements such as paper.

Figure 2:
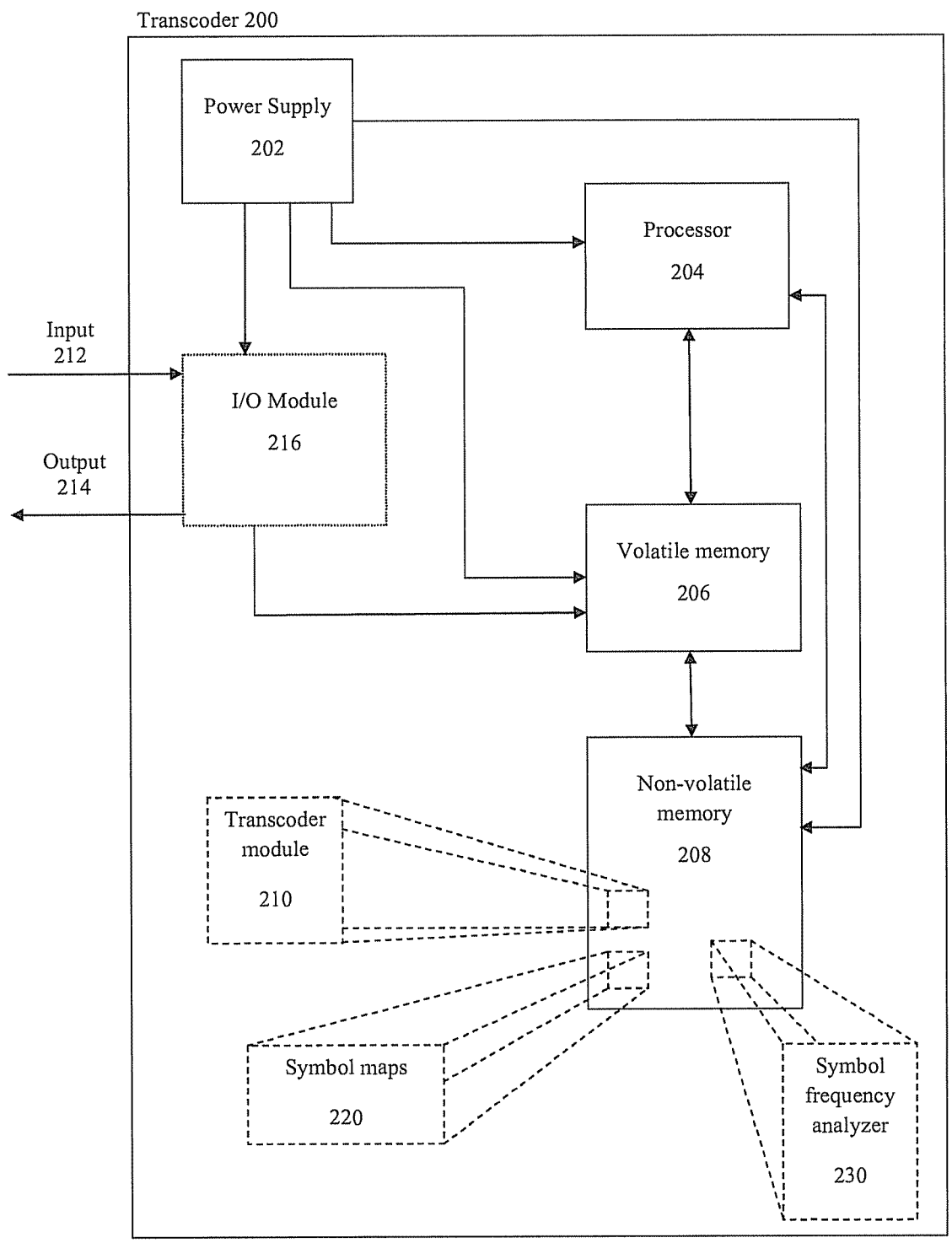
FIG. 2 is a block diagram of an exemplary transcoder configured to encode an input human readable symbol sequence into a codon sequence with a low probability of biological impact.

FIG. 2 is a block diagram of an exemplary transcoder 200 configured to encode an input symbol sequence into a codon sequence such that the codon sequence has substantially no biological impact on a host organism if introduced into the organism as a synthetic nucleic acid sequence (e.g., as free DNA). The transcoder 200 may also be configured to decode an input sequence of codons and thereby yield the originally input symbol sequence. Thus, the exemplary transcoder 200 depicted in FIG. 2 may be used to both encode a human readable symbol sequence into a codon sequence, and to decode a codon sequence into a human readable symbol sequence.

The power supply 202 provides a source of power to modules disposed within the transcoder 200. In some embodiments, power is supplied externally by one or more conductive wires, for example, by a power or serial bus cable. In other embodiments, a battery may be used as a source of power. In other embodiments, a human brain is used as a power source.

One or more processors 204 are adapted to execute sequences of instructions by loading data from and storing data to a local memory module (for example, volatile memory 206, which may be implemented as any combination of static and/or dynamic RAM). Possible instructions may include, without limitation, instructions for data conversions, formatting operations, arithmetic operations, communication instructions, and/or storage and retrieval operations.

One or more I/O modules 216 may be used to interface a set of I/O peripherals with various programs, processes, or applications executing within the volatile memory 206 of the transcoder 200. In some embodiments, the I/O modules 216 may consist of one or more device drivers adapted to interface a set of hardware devices with an operating system associated with the transcoder 200. Note that the I/O modules 216 may be implemented as any combination of software, firmware, or hardware according to embodiments described herein.

A wide variety of input peripherals may be used to generate input 212 to the transcoder 200 according to embodiments disclosed herein. These input peripherals include, without limitation, keyboards, mice, trackballs, touch panels, microphones, controllers (e.g., joysticks), scanners, digital cameras, pencils, pens, markers, crayons, and communicative interfaces for networked devices (e.g., network or serial bus interfaces).

Similarly, a wide variety of output peripherals may be used to write and/or display output 214 according to various embodiments disclosed herein. These output peripherals include, without limitation, display devices (e.g., monitors), printers, projectors, televisions, speakers, local memory modules, pencils, pens, markers, crayons, and networked devices (e.g., computers, digital cameras, personal data assistants, remote memory devices, high-speed serial bus devices, etc.).

A non-volatile memory module 208 may be used to persistently store data, instructions, process states, memory tables, and other information within the transcoder 200. The non-volatile memory module 208 may be implemented as any type or combination of memory adapted for persistent storage, including, without limitation, conventional hard disks, ROM (e.g., PROM, EPROM, EEPROM), flash memory, paper, etc. Note also that in some embodiments, all or a portion of the non-volatile memory module 208 may serve as virtual memory for the volatile memory module 206.

In some embodiments, the non-volatile memory 208 may include a symbol frequency analyzer 230 for determining how frequently certain symbols appear within one or more input symbol streams. For example, the symbol frequency analyzer 230 may be used to determine that the symbol "v" has a frequency of occurrence of approximately 1% within a specified symbol stream, while the symbol "e" has a frequency of occurrence of approximately 13% within the same stream. Note that an exemplary process of implementing the symbol frequency analyzer 230 has been described in more detail below (see FIG. 4 and accompanying text).

In some embodiments, the non-volatile memory 208 may include one or more symbol maps 220 which may be used to construct synthetic nucleic acid sequences with low probabilities of biological impact. An exemplary symbol map 220 has been provided with reference to FIG. 3. As shown by this figure, each symbol 304 from a domain of possible symbols (including letters, numbers, punctuation marks, symbols, and control symbols) uniquely maps to a single codon identifier 302. The symbol maps 220 may thus be used to translate a sequence of human readable symbols into a sequence of codons, or to translate a sequence of codons into a sequence of human readable symbols.

Note that while the symbol map 220 depicted in FIG. 3 illustrates a one-to-one mapping of sixty-four possible symbols 304 to sixty-four possible codons identifiers 302, the symbol map 220 depicted in FIG. 3 is merely exemplary in nature, and has been included herein so as to illustrate the broader principles of the application. It is to be understood that embodiments disclosed herein encompass a wide variety of possible mappings. Moreover, the domain of possible symbols 304 and the range of possible codon identifiers 302 can also be smaller than or larger than sixty-four.

In some embodiments, for example, a reduced symbol domain may be utilized in order to further decrease the probability that a constructed synthetic nucleic acid sequence will have a detectable biologically impact an organism. This may be implemented, for example, by excluding from the symbol map 220 those permutations of nucleotides which could potentially be interpreted as a start codon by an organism's internal biological processes (ATG, GTA, *AT, TG*, etc.).

In other embodiments, the symbol domain may be expanded in order to support a larger number of encodable symbols (for example, upper-case and lower-case symbols, non-standard symbols, etc.). This may be implemented, for example, by mapping each symbol 304 into a set of multiple codons instead of a single codon (for example, "A"=CAGCCG).

Returning now to FIG. 2, the non-volatile memory 208 may also include a transcoder module 210 for translating a sequence of symbols 304 into a sequence of codon identifiers 302 and/or for translating a sequence of codon identifiers 302 into a sequence of symbols. In some embodiments, the transcoder module 210 may utilize one or more symbol maps 220 as an input argument, value, or parameter. In other embodiments, the transcoder module 210 may contain internal logic supplying one or more encoding schemes (e.g., switch and/or case logic). Note that an exemplary process of encoding a sequence of symbols 304 into a sequence of codon identifiers 302 has been provided below with reference to FIG. 5, while an exemplary process of decoding a sequence of codon identifiers 302 into a sequence of symbols 304 has been provided below with reference to FIG. 6.

Figure 4:
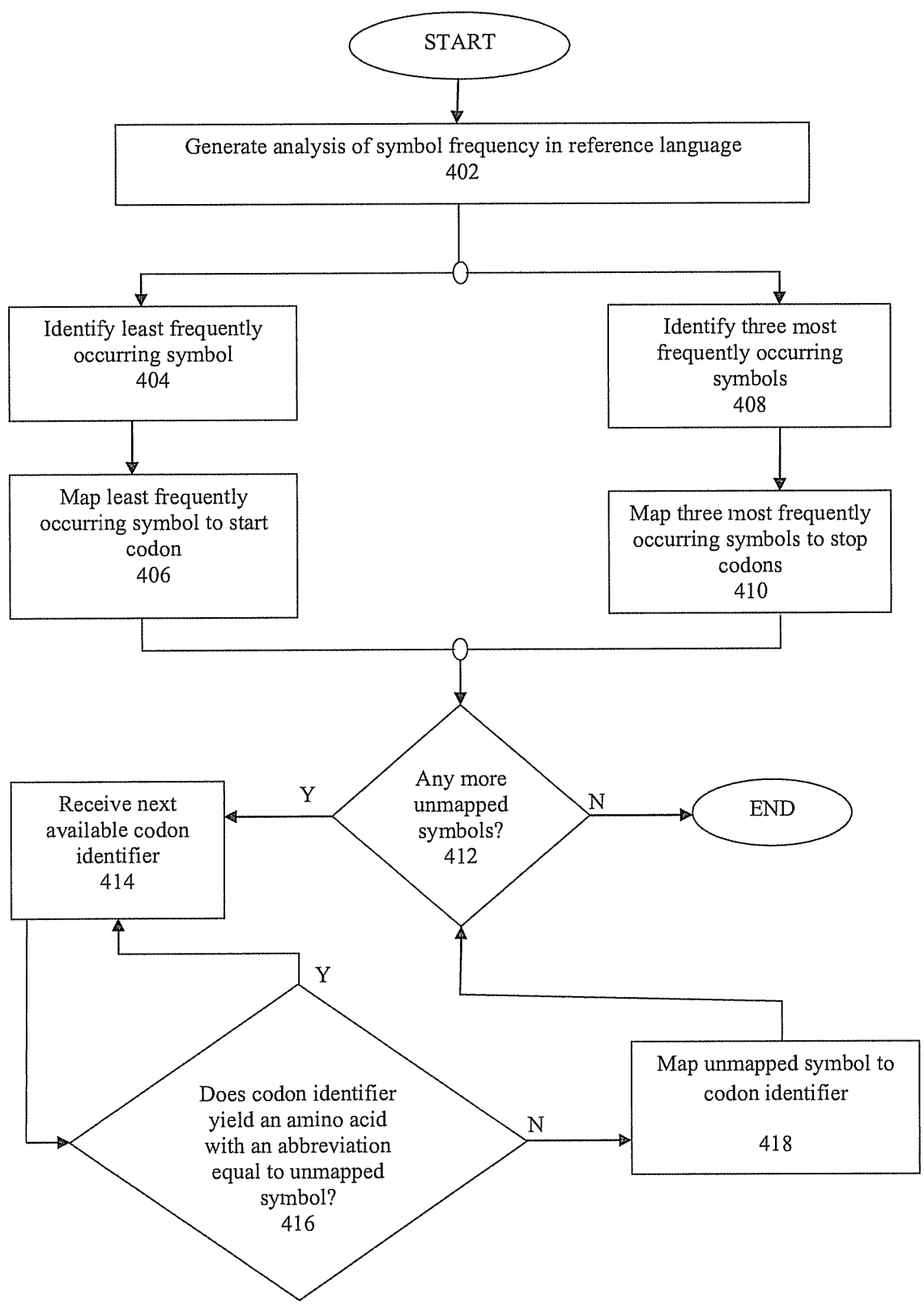
FIG. 4 is a flow diagram of an exemplary method of creating a human readable symbol map which may be used to generate a nucleic acid sequence with a low probability of biological impact.

FIG. 4 is a flow diagram of an exemplary method of creating a symbol map which may be used to generate a nucleic acid sequence with a substantially reduced or a low probability of biological impact.

At block 402, an analysis of symbol frequency in a reference language or symbol stream is generated. This may be accomplished, for example, by parsing one or more input streams in order to determine the number of occurrences of a certain symbol relative to the total number of symbols analyzed. In some embodiments, a counter may be assigned to each unique symbol that is discovered within the one or more input streams. In other embodiments, counters may be assigned to only those symbols that are elements of an input symbol domain. Note that lower-case and upper-case equivalents may be treated as the same or separate symbols.

At block 404, the least frequently occurring symbol within the symbol domain may be determined. This may be accomplished, for example, by conventional sort routines (for example, bubble sort, insertion sort, selection sort, quick sort, etc.). In some embodiments, the least frequently occurring symbol is the asterisk symbol "*". Note, however, that the least frequently occurring symbol may depend upon the one or more input streams analyzed and/or the symbol domain selected.

At block 406, the least frequently occurring symbol may be mapped to a specific permutation of nucleotides known as the start codon (i.e., ATG). A start codon is commonly used by an organism's internal processes to indicate the beginning of a coding sequence. Mapping the least frequently occurring symbol to the start codon in this manner substantially reduces the number of start codons that will appear within the encoded sequence, thereby reducing the likelihood that an cell's internal processes will interpret a portion of the encoded sequence as a genetic instruction.

At block 408, the three most frequently occurring symbols within the symbol domain may be determined. This may be implemented, for example, by reading the three most frequently occurring symbols within a symbol list that has been sorted by occurrence frequency (for example, by reading the sorted list generated at block 404). In some embodiments, the three most frequently occurring symbols are the letters "E", "A", and "T" (where the frequencies of upper-case and lower-case equivalents have been aggregated). As in the prior case, the three most frequently occurring symbols may depend upon the one or more input streams analyzed and/or the symbol domain selected.

At block 410, each of the three most frequently occurring symbols may then be mapped to a respective stop codon (i.e., TAA, TAG, and TGA). Mapping the most frequently occurring symbols to stop codons in this manner increases the likelihood that a stop instruction will appear within a given sequence of nucleotides, thereby substantially reducing the likelihood that an cell's internal processes will interpret a portion of the encoded sequence as a genetic instruction.

Each unmapped symbol from the symbol domain may then be mapped to a codon identifier that has not yet been mapped to a human readable symbol. Optionally, logic may also be provided that is configured to prevent an unmapped symbol from mapping to a codon that generates an amino acid which has a single-letter abbreviation that is equivalent to the unmapped symbol. For example, if the next unmapped symbol were the letter "V", the codons "GTT", "GTC", "GTA", and "GTG" may be excluded from the range of possible candidates that could map to "V", since each of these codons may ultimately yield the amino acid valine (commonly abbreviated as "V"). Exemplary logic for accomplishing this functionality is discussed below with reference to blocks 412-418.

At block 412, a decision may be made as to whether an unmapped human readable symbol presently exists. If there are no unmapped symbols remaining, the process can end. Otherwise, the next unmapped symbol may be retrieved and the process continued at block 414.

The next available codon identifier may then be determined at block 414. This may be implemented by retrieving the next codon identifier from a reference data structure (e.g., array, list, heap, stack, queue, etc.).

A decision may then be made at block 416 as to whether the next available codon identifier yields an amino acid with an abbreviation that is equivalent to the unmapped symbol. In some embodiments, both upper and lower case equivalents are considered in this decision. If the codon identifier does in fact yield an amino acid with an abbreviation that is equivalent to the unmapped symbol, a new codon identifier may be received at block 414, and the process may repeat until a suitable codon identifier is discovered. Otherwise, if the codon identifier does not yield an amino acid with an abbreviation that is equivalent to the unmapped symbol, the unmapped symbol may be mapped to the selected codon identifier at block 418, and the process repeated per block 412.

Note that in cases where each of the remaining unmapped codon identifiers yield an amino acid with an abbreviation that is equivalent to the unmapped symbol, conventional processes of backtracking may be utilized in order to unmap and reassign previous symbols to alternate codon identifiers. In other embodiments, symbols with amino acid abbreviation equivalents may be mapped to codon identifiers before any other symbols are mapped, thereby obviating the need for backtracking logic.

Figure 5:
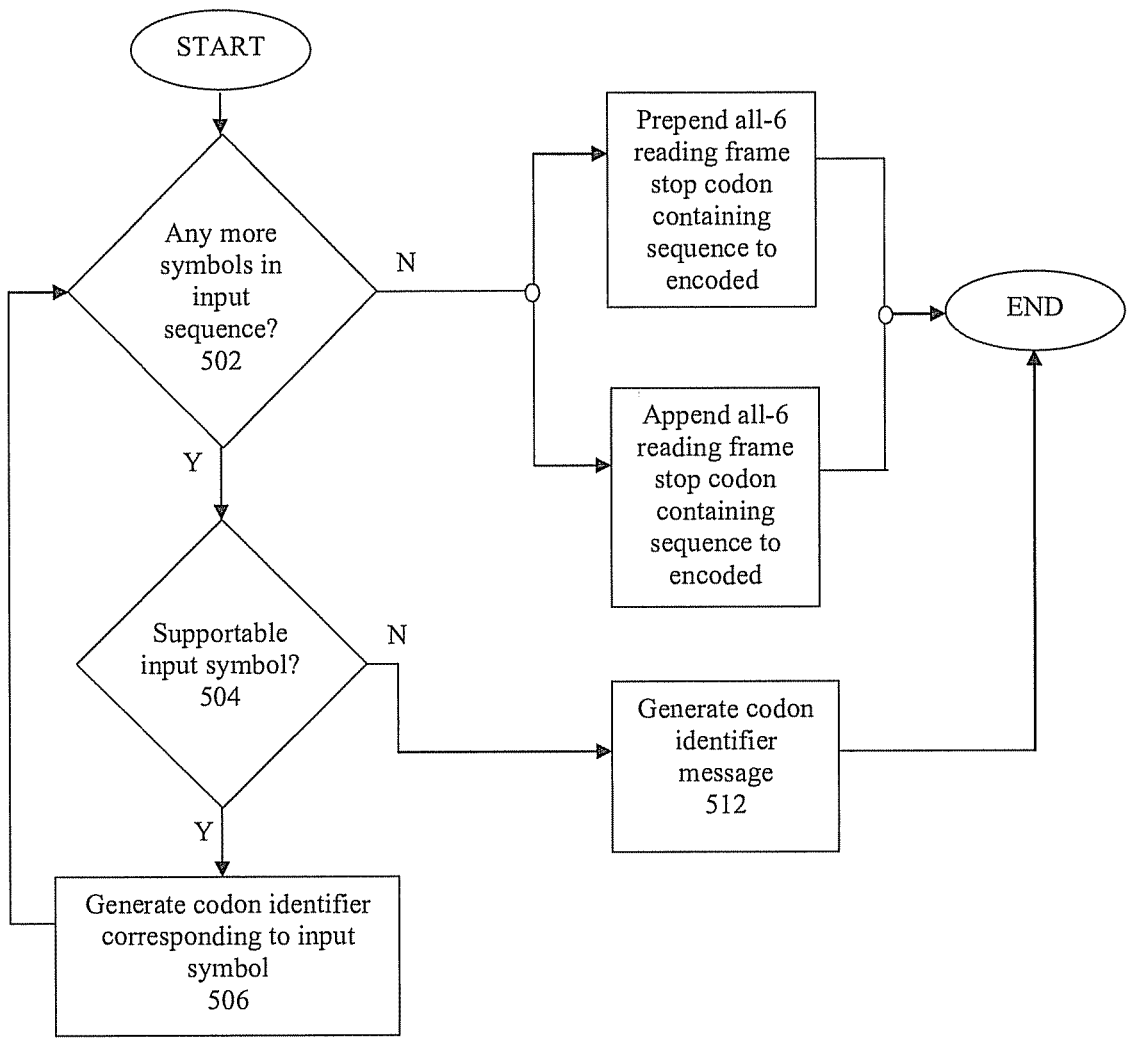
FIG. 5 is a flow diagram of an exemplary method of encoding an input human readable symbol sequence into a codon sequence with a low probability of biological impact.

FIG. 5 is a flow diagram of an exemplary method of encoding an input symbol sequence into a codon sequence with a low probability of biological impact.

At block 502, a decision is made as to whether an un-encoded symbol still exists within the input symbol sequence. If all human readable symbols from the input symbol sequence have been encoded, the process can end according to some embodiments. Alternatively, the process may further comprise inserting an all-6 reading frame stop codon at the beginning and/or end of the encoded sequence. This is shown at blocks 508 and 510, respectively. These all-6 reading frame stop codons may thus serve to designate the beginning and/or end of an encoded message, thereby allowing a message to be more easily detected among a large stream of successive nucleotides.

In some embodiments, the all-6 reading frame stop codons may be used to further decrease the probability that a cell's internal processes or a virus will interpret a portion of the encoded sequence as a genetic instruction. In some embodiments, for example, one or more all-6 reading frame stop codons may be interleaved within the encoded message at periodic intervals, thereby ensuring that a stop codon occurs every "n" reading frames. A transcoder adapted to decode such a message may simply ignore these codons during the decoding process.

If an unencoded symbol still exists within the input sequence, at block 504, a decision may be made as to whether the input symbol is supportable (i.e., whether it exists within the domain of encodable symbols). In some embodiments, an error message may be generated when it is determined that a certain symbol cannot be encoded (e.g., as shown at block 512). In other embodiments, any non-encodable symbols may simply be ignored. In still other embodiments, a special symbol may be used to indicate that an unencodable symbol has been identified. This special symbol can thus serve as a replacement for every unencodable symbol encountered within the input symbol sequence.

At block 506, the codon identifier which corresponds to the input symbol can then be generated. According to some embodiments, the codon identifier which corresponds to the input symbol can be determined by consulting a symbol map that is stored within a local memory source (e.g., the symbol maps 220 depicted in FIG. 2 and FIG. 3). The process may then repeat at block 502 until all input symbols have finally been encoded.

Figure 6:
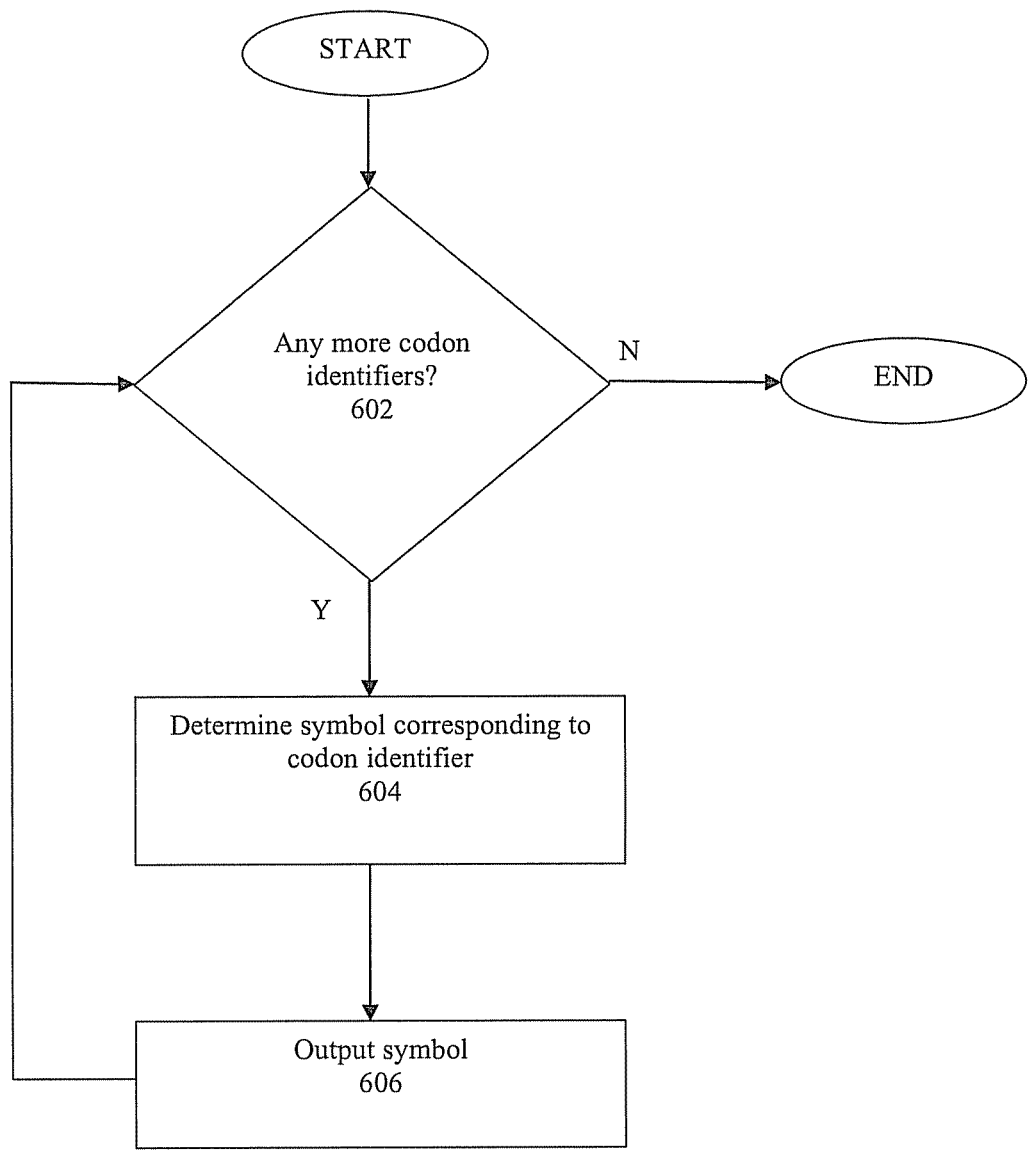
FIG. 6 is a flow diagram of an exemplary method of decoding a nucleic acid sequence with a low probability of biological impact into a human readable symbol sequence.

FIG. 6 is a flow diagram of an exemplary method of decoding a nucleic acid sequence with a low probability of biological impact into a symbol sequence.

At block 602, a decision is made as to whether any additional codon identifiers exist within an input sequence of codon identifiers. If no codon identifiers exist, the process may then end. Otherwise, the process may continue per block 604. This process would be repeated for all three 5' reading frames.

The symbol corresponding to the codon identifier may then be determined at block 604. According to some embodiments, the symbol which corresponds to the codon identifier may be determined by consulting a symbol map that is stored within a local memory source (e.g., the symbol maps 220 depicted in FIG. 2 and FIG. 3).

The determined symbol may then be output at block 606. In some embodiments, the symbol may be written to, or displayed upon, a connected output peripheral (for example, a display device, printer, television screen, paper, etc.). In other embodiments, the symbol may be written to a local memory source and/or stored within one or more files. In some embodiments, (for example, as that shown in FIG. 6) symbols may be output as soon as they are determined. In other embodiments, the output may be generated after all symbols have been determined.

Figure 7:
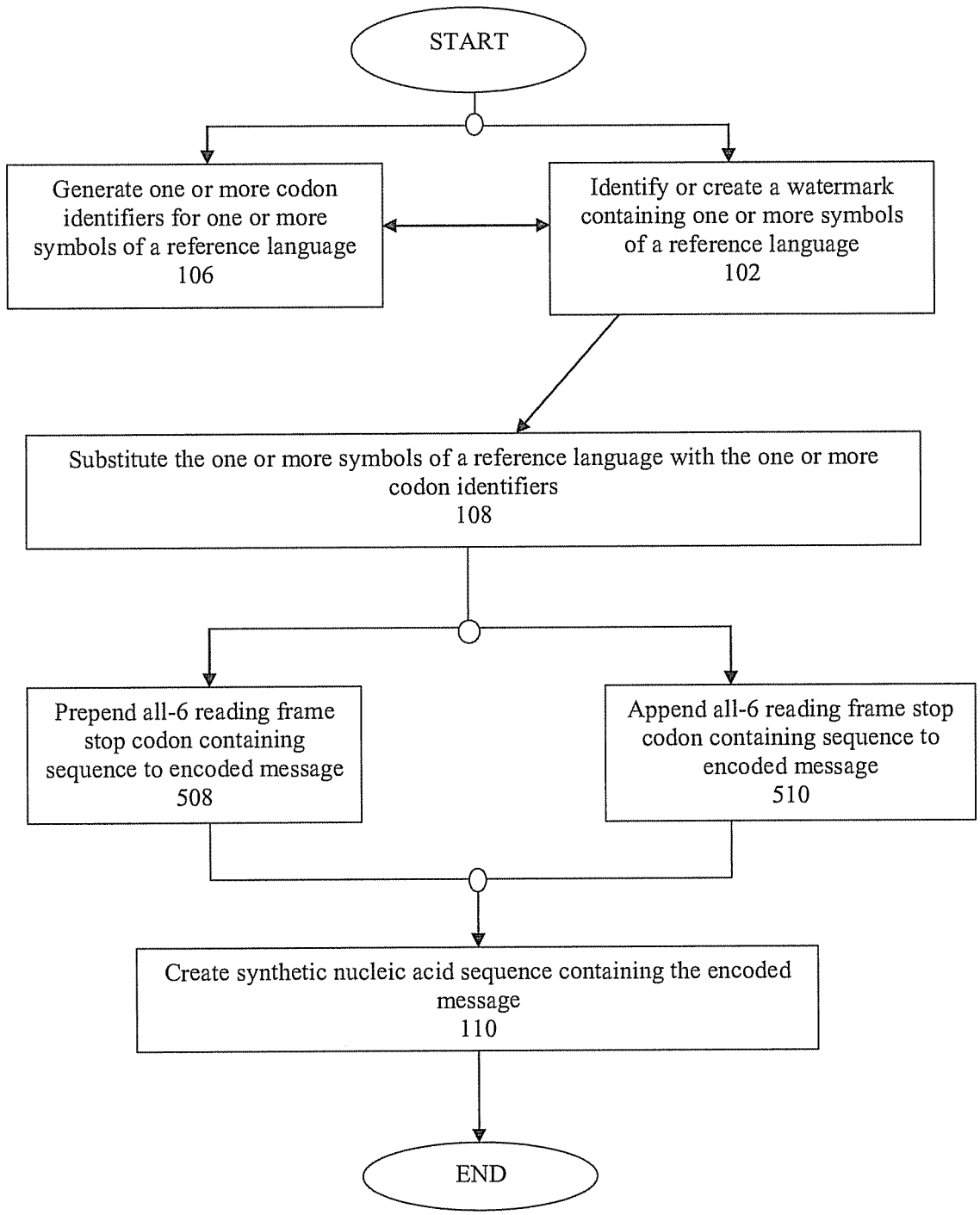
FIG. 7 is a flow diagram of an exemplary method of encoding a watermark into a synthetic nucleic acid sequence with a low probability of biological impact.

FIG. 7 is a flow diagram of an exemplary method of encoding a watermark into a synthetic nucleic acid sequence with a low probability of biological impact. Each symbol from a reference language can be assigned a codon identifier 106. A watermark containing a series of symbols from a reference language can be generated 102. Each symbol in the watermark can be substituted with a codon identifier and the resulting encoded sequence can be prepended with an all-6 reading frame stop codon containing sequence 508 and appended with an all-6 reading frame stop codon containing sequence 510 to create a synthetic nucleic acid sequence containing the encoded watermark message 110. Thus, within the context of a series of codon identifiers that are used to encode a message that exists between all-an all-6 reading frame stop codon containing sequence 5' to a first codon identifier in the sequence and an all-6 reading frame stop codon containing sequence 3' to the last codon identifier in the sequence, it would be possible to map symbols to codon identifiers which may represent a single letter abbreviation of an amino acid. In this context, it would be understood that the all-6 reading frame stop codon containing sequences would prevent an encoded message containing an amino acid abbreviation from being read as genetic material. Thus, a more static code that would typically not change from implementation to implementation can be created. Such a code can then become a standard such as a file format.

FIGS. 8A-8E illustrate an exemplary embodiment contemplated for use with the system described above.

Synthetic Nucleic Acid Sequences

Messages can be input as synthetic nucleic acid fragments into a cell or virus and incorporated into a gene, a genome, a plasmid, or a chromosome, or any other genetic material in a cell. Incorporated nucleic acids are made up of codon identifiers that represent a series of human readable symbols from a human reference language. The sequence of codon identifiers creates a non-genetic message or watermark that can be used to identify or authenticate any cell or virus containing that message.

A synthetic nucleic acid sequence can further comprise an all-6 reading frame stop codon containing sequence 5' (prior to) to a first codon identifier in the sequence, an all-6 reading frame stop codon containing sequence 3' (subsequent to) to the last codon identifier in the sequence, or both.

Provided herein is a synthetic nucleic acid sequence, wherein said synthetic nucleic acid sequence comprises one or more codon identifiers corresponding to a set of human readable symbols of a reference language that conveys a non-genetic message, and further wherein said synthetic nucleic acid sequence is not genetically viable and does not have a biological impact upon a recombinant or synthetic cell, or upon a recombinant or synthetic virus, comprising the synthetic nucleic acid sequence.

In one embodiment, a synthetic nucleic acid sequence cannot be biologically translated into a functional amino acid sequence by the recombinant or synthetic cell/virus.

The one or more codon identifiers do not correspond to sequence of a gene or other biologically active sequence. Rather, the one or more codon identifiers correspond to one or more letters, one or more numbers, one or more spaces, one or more punctuation marks (e.g., " , . ; [ ] { } ( ) : ! ? and '), one or more mathematical symbols (#, (, ), ?, *, +, =, $, %, etc.), one or more typographical characters (e.g., @, ©, ™, ®, §, etc.), one or more new lines, or a combination of any thereof and are made up of three nucleotides.

In one aspect, the set of human readable symbols comprises a watermark. Watermarks include, but are not limited to, a copyright notice, a trademark, a company identifier, a name, a phrase, a sentence, a quotation, genetic information, unique identifying information, data, digital computer instructions, texts, graphics, video, information intended to be operated upon by a DNA-based computer, or a combination of any thereof.

The synthetic nucleic acid sequence can further comprise an all-6 reading frame stop codon containing sequence 5' to a first codon identifier in the sequence, an all-6 reading frame stop codon containing sequence 3' to the last codon identifier in the sequence, or both.

One can empirically determine the size of a watermark based on the size of one or more of the following: a gene, a genome, a plasmid, an artificial chromosome, a cell, or an organism. Message lengths can be up to about 40 Kb, up to about 35 Kb, up to about 30 Kb, up to about 25 Kb, up to about 20 Kb, up to about 15 Kb, up to about 10 Kb, up to about 5 Kb, up to about 3 Kb, up to about 2 Kb, up to about 1 Kb, up to about 0.5 Kb, up to about 0.1 Kb, or any value there between. In one embodiment, a message length can be up to about 5 Kb. In another embodiment, a message length can be up to about 2 Kb. A message length, typically, does not exceed the length of a gene, genome, plasmid, or chromosome into which it is to be incorporated or replace.

Recombinant and Synthetic Cells, Viruses, Organisms and Animals

One would understand that synthetic nucleic acid sequences conveying non-genetic messages can be used in any type of cell. In some instances, cells can be present in a population of cells (e.g., a cell culture, an embryo, a multicellular organism, a plant, an animal, etc.).

Provided herein is a recombinant or synthetic cell containing a synthetic nucleic acid sequence described herein. A recombinant or synthetic cell can be a prokaryotic cell, a eukaryotic cell, or an archaeal cell. Also provided herein is a recombinant or synthetic virus, multicellular organism, or animal containing a synthetic nucleic acid sequence described herein. A set of human readable symbols can be a watermark that allows the authentication or identification of said recombinant or synthetic cell, virus, organism or animal; or identification of an organism comprising recombinant or synthetic cells or viruses.

The recombinant or synthetic cells described herein are useful for tracking of cells or organisms for research and/or commercial use. Cells also include, but are not limited to cells and organisms in a research laboratory. Such cells and organisms may be distributed internally within a company or institute, or distributed externally as part of a collaboration or material transfer agreement. Other cells are described below with respect to samples which can be assessed for cells or organisms containing a watermark.

Provided herein is a recombinant animal that contains a synthetic nucleic acid sequence conveying a non-genetic message or watermark. Recombinant animals include, for example, transgenic rodents (e.g., mice, rats, ferrits, rabbits, etc.), horses (e.g., pure-bred, hybrid breed or thoroughbred), cows, bulls, dogs, cats, sheep, primates (e.g., gorillas, chimpanzees, monkeys, orangutans, etc.), fish (e.g., zebra fish or exotic fish), amphibians (e.g., frogs), insects, etc. Such watermarks can be used to identify, for example, the source of the animal, or identification of a specific genetic modification.

Provided herein is a recombinant embryo that contains a watermark; such watermarks can be used to track and identify embryos based on encoded information.

Also provided herein is a recombinant plant that contains a watermark; such watermarks can be used to track and identify plants based on encoded information.

A recombinant or synthetic cell can be a prokaryotic cell, a eukaryotic cell, or an archaeal cell.

A prokaryotic cell can be, for example, a bacterial cell that is Gram-positive or Gram-negative.

A eukaryotic cell can be, for example, a yeast cell, a fungal cell, an algal cell, an animal cell, or a plant cell.

Prokaryotic Cells

A prokaryotic cell can be, for example, a bacterial cell that is Gram positive or Gram negative, or may lack a cell wall. A synthetic nucleic acid sequence can be incorporated in a genome, a plasmid, or an artificial chromosome of any Gram-negative or Gram-positive bacterium.

Gram-negative bacterium include, but are not limited to Enterobacteriaceae spp. (e.g., *E. coli*, *E. cloacae*, *E. intermedius*, etc.), *Hemophilus* spp. (e.g., *H. influenzae*, etc.), Vibrionaceae spp. (e.g., *V. cholera*, etc.), Pseudomonadaceae spp. (e.g., *Pseudomonas aeruginosa*, *Pseudomonas fluorescens*, *Pseudomonas putida*, *Pseudomonas stutzeri*, etc.), *Helicobacter* spp. (e.g., *H. pylori*, etc.), *Synechosystis* spp, *Acinetobacter baumannii*, *Acidovorax delafieldii*, *Aeromonas veronii*, *Aquaspirrilium* spp., *Bordetella bronchiseptica*, *Flavobacterium odoratum*, *Cryseobacterium gleum*, *Citrobacter braaki*, *Citrobacter freundii*, *Comamonas (Delftia) acidovorans*, *Burkholderia cepacia*, *Yersinia kristensenii*, *Stenotrophomonas* spp., *Serratia* spp. (e.g., *Serratia liquefaciens*, *Serratia marcescens*, etc.), *Salmonella* spp. (e.g., *Salmonella typhimurium*, etc.), *Ralstonia* spp. (e.g., *Ralstonia eutropha*, *Ralstonia pickett*, etc.), *Proteus vulgaris*, *Providencia rettgeri*, *Pseudomonas* spp. *Pantoea ananas*, *Paracoccus marcusii*, *Ochrobactrum anthropi*, *Morganella morganii*, *Neisseria* spp. (e.g., *Neisseria meningitides*, etc.), *Klebsiella* spp. (e.g., *Klebsiella oxytoca*, *Klebsiella pneumonia*, etc.) and *Hydrogenophaga palleronii*. One would understand that other genus and species of gram negative bacteria are included herein.

Gram-positive bacteria include, but are not limited to, *Streptococcus* spp. (e.g., *S. pneumoniae*, *S. sanguis*, etc.), *Enterococci* spp. (e.g., *E. faecalis*, etc.), *Bacterioides* spp. and *Clostridia* spp. (e.g., *C. sporogenes*, etc.), *Mycobacterium* spp. (e.g., *M. tuberculosis, M. avium*, etc.), *Corynebacterum* spp. (e.g., *C. renale*, etc.), *Peptostreptococus* spp., *Listeria* spp. (e.g., *L. monocytogenes*, etc.), *Legionella* spp., *Alicyclobacillus acidocaldarius*, *Bacillus* spp. (e.g., *Bacillus licheniformis*, *Bacillus pumilus*, *Bacillus sphaericus*, *Bacillus subtilis*, *Bacillus thuringensis*, *Bacillus cereus*, *Bacillus circulans*, *Bacillus dipsosauri*, etc.), *Brevibacillus choshinensis*, *Brevibacterium brevis*, *Deinococcus radiodurans*, *Staphylococcus* spp. (e.g., *Staphylococcus aureus*, *Staphylococcus auricularis*, *Staphylococcus capitis*, *Staphylococcus epidermidis*, etc.), *Rhodococcus equi*, *Propionibacterium acnes*, *Paenibacillus* spp. (e.g., *Paenibacillus glucanolyticus*, *Paenibacillus polymyxa*, etc.), *Kocuria rosea*, *Microbacterium saperdae*, *Micrococcus* species, *Kocuria* spp. (e.g., *Kocuria kristinae*, *Kocuria rhizophila*, etc.), and *Geobacillus sterothermophilus*. One would understand that other genus and species of gram positive bacteria are included herein.

Bacteria lacking a defined cell wall include, but are not limited to, *Mycoplasma* spp. (e.g., *M. capricolum*, *M. gallisepticum*, *M. genitalium*, *M. hominis*, *M. hyopneumoniae*, *M. laboratorium*, *M. mycoides*, *M. ovipneumonia*, *M. pneumoniae*, etc.).

In some embodiments, photosynthetic bacteria, including for example, green sulfur bacteria, purple sulfur bacteria, green nonsulfur bacteria, purple nonsulfur bacteria, or cyanobacteria may be used. Cyanobacterial species that can be used include, without limitation, *Agmenellum*, *Anabaena*, *Anabaenopsis*, *Anacystis*, *Aphanizomenon*, *Arthrospira*, *Asterocapsa*, *Borzia*, *Calothrix*, *Chamaesiphon*, *Chlorogloeopsis*, *Chroococcidiopsis*, *Chroococcus*, *Crinalium*, *Cyanobacterium*, *Cyanobium*, *Cyanocystis*, *Cyanospira*, *Cyanothece*, *Cylindrospermopsis*, *Cylindrospermum*, *Dactylococcopsis*, *Dermocarpella*, *Fischerella*, *Fremyella*, *Geitleria*, *Geitlerinema*, *Gloeobacter*, *Gloeocapsa*, *Gloeothece*, *Halospirulina*, *Iyengariella*, *Leptolyngbya*, *Limnothrix*, *Lyngbya*, *Microcoleus*, *Microcystis*, *Myxosarcina*, *Nodularia*, *Nostoc*, *Nostochopsis*, *Oscillatoria*, *Phormidium*, *Planktothrix*, *Pleurocapsa*, *Prochlorococcus*, *Prochloron*, *Prochlorothrix*, *Pseudanabaena*, *Rivularia*, *Schizothrix*, *Scytonema*, *Spirulina*, *Stanieria*, *Starria*, *Stigonema*, *Symploca*, *Synechococcus*, *Synechocystis*, *Tolypothrix*, *Trichodesmium*, *Tychonema*, or *Xenococcus* species.

Each of the aforementioned prokaryotic cells and others known in the art are contemplated for use herein.

Archaea

Archaea are a group of single-celled microorganisms. They have no cell nucleus or any other organelles within their cells. Archaea include, but are not limited to cells of the phyla: Crenarchaeota, Euryarchaeota, Korachaeota, Nanoacraeota and Thaumarchaeota. Each of the aforementioned archaea and others known in the art are contemplated for use herein.

Viruses

Viruses are typically classified into the following groups: I: dsDNA viruses (e.g., Adenoviruses, Herpesviruses, Poxviruses); II: ssDNA viruses (+)sense DNA (e.g., Parvoviruses); III: dsRNA viruses (e.g., Reoviruses); IV: (+)ssRNA viruses (+)sense RNA (e.g., Picornaviruses, Togaviruses); V: (−)ssRNA viruses (−)sense RNA (e.g., Orthomyxoviruses, Rhabdoviruses); VI: ssRNA-RT viruses (+)sense RNA with DNA intermediate in life-cycle (e.g., Retroviruses); and VII: dsDNA-RT viruses (e.g., Hepadnaviruses).

Each of the aforementioned viruses and others known in the art are contemplated for use herein.

Eukaryotic Cells

A eukaryotic cell contemplated herein can be any cell with a nucleus enclosed within a cell membrane, for example, a yeast cell, a fungal cell, an algal cell, an animal cell, or a plant cell.

Yeast

Yeast are unicellular microorganisms that belong to one of three classes: Ascomycetes, Basidiomycetes and Fungi Imperfecti. Pathogenic yeast strains and nonpathogenic yeast strains are considered herein.

Genera of yeast strains include, but are not limited to, *Saccharomyces, Candida, Cryptococcus, Hansenula, Kluyveromyces, Pichia, Rhodotorula, Schizosaccharomyces* and *Yarrowia*.

Non-limiting representative species of yeast strains include *Saccharomyces cerevisiae, Saccharomyces carlsbergensis, Candida albicans, Candida kefyr, Candida tropicalis, Candida guillermondii, Candida parapilosis, Cryptococcus laurentii, Cryptococcus neoformans, Cryptococcus humicolus, Hansenula anomala, Hansenula polymorpha, Kluyveromyces Kluyveromyces lactis, Kluyveromyces marxianus* var. *lactis, Pichia pastoris, Rhodotorula rubra, Rhodotorula glutinous, Schizosaccharomyces pombe* and *Yarrowia lipolytica*. It is understood that a number of these species include a variety of subspecies, types, subtypes, etc. that are meant to be included within the aforementioned species.

Each of the aforementioned yeast genera and species and others known in the art are contemplated for use herein.

Algae

A synthetic nucleic acid sequence can be incorporated in a genome, a plasmid, or an artificial chromosome of any algal species.

Algae that can be used in the methods of the invention can be any algae, and can include microalgae, such as but not limited to, *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Platymonas, Pleurochiysis, Pleurococcus, Prototheca, Pseudochlorella, Pyramimonas, Pyrobotrys, Scenedesmus, Schizochytrium, Skeletonema, Spyrogyra, Stichococcus, Tetraselmis, Thraustochytrium, Thalassiosira, Viridiella*, or *Volvox* species.

Each of the aforementioned algae and others known in the art are contemplated for use herein.

Plant Cells

Plant cells that can be used include those obtained from organisms such as trees, herbs, bushes, grasses, vines, ferns, and mosses. Diversity of living plant divisions includes non-vascular land plants or bryophtes, such as Marchantiophyta (liverworts), Anthocerotophyta (hornworts), Bryophyta (mosses) and Horneophytopsida; and vascular plants or tracheophytes, such as Rhyniophyta, Zosterophyllophyta, Lycopodiophyta (club mosses), Trimerophytophyta, Pteridophyta (ferns, whisk ferns & horsetails), Progymnospermophyta, and Seed plants or spermatophytes, such as Pteridospermatophyta (seed ferns), Pinophyta (conifers), Cycadophyta (cycads), Ginkgophyta (ginkgo), Gnetophyta (gnetophytes), and Magnoliophyta (flowering plants).

Each of the aforementioned plant cells and others known in the art are contemplated for use herein.

Animal Cells

Animal cells that can be used include, but are not limited to vertebrates, such as fish, amphibians, reptiles, birds and mammals (e.g., rodents, primates, sheep, horses, cows, pigs, dogs, cats, etc.); arthropods, such as insects (e.g., *Drosophila melanogaster*); and nematodes (e.g., *Caenorhabditis elegans*).

Each of the aforementioned animal cells and others known in the art are contemplated for use herein.

Fungii

Fungii that can be used include any of the phyla Microsporidia, Chytridiomycota, Blastocladiomycota, Neocallimastigomycota, Glomeromycota, Ascomycota, and Basidiomycota. Exemplary genera of fungi to be used in the compositions and methods described herein include, for example, *Pullularia, Chaetomium, Aspergillus, Coniophora, Pseudocercosporella, Helminthosporium, Pyrenophorae, Septoria, Helminthosporium, Fusarium, Rhizoctonia, Cercospora, Peronospora, Erysiphe, Pythium*, and *Pestalozzia*.

Species of fungi contemplated for use in the compositions and methods described herein include, for example, *Pseudocercosporella herpotrichoides, Helminthosporium gramineum, Pyrenophorae avenae, Septoria nodorum, Helminthosporium teres, Fusarium roseum, Fusarium nivale, Fusarium culmorum, Rhizoctonia cerealis, Pullularia pullulans, Chaetomium globosum, Coniophora puteana, Cercospora beticola, Peronospora tabacina, Erysiphe cichoracearum, Pyprenophora avenae, Whetzelinia sclerotiorium, Monilia laxa, Mycosphaerella fijiensis, Marssonina panattoniana, Alternaria solani, Aspergillus niger, Cladosporium herbarium, Penicillium expansum, Phialophora cinerescens, Phoma betae, Phoma foveata, Phoma lingam, Verticillium dahliae, Ascochyta pisi, Guignardia bidwellii, Corticium rolfsii, Phomopsis viticola, Sclerotinia sclerotiorum, Sclerotiniia minor, Phytophthora cinnamomi, Phytophthora cactorum, Phytophthora capsici, Phytophthora parasitica, Phytophthora megasperma, Phytophthora syringae, Coryneum cardinal, Septoria tritici, Botrytis cinerea, Fusarium oxysporum, Fusarium melonis, Rhizoctonia solani*, and *Helminthosporium gramineum*.

Each of the aforementioned fungii and others known in the art are contemplated for use herein.

Methods of Creating a Recombinant or Synthetic Cell or Virus

Provided herein is a method of creating a recombinant or synthetic cell or virus comprising a watermark, comprising: (i) generating a nucleic acid sequence comprising a sequence of codon identifiers selected based upon the text of the watermark such that the symbol mapping maps codon identifiers corresponding to start codon(s) to human readable symbols that possess a disproportionally low frequency in the language of the watermark, and maps codon identifiers corresponding to stop codon(s) to human readable symbols that possess a disproportionally high frequency in the language of the watermark; (ii) synthesizing said nucleic acid sequence; and (iii) introducing said nucleic acid sequence into a recombinant or synthetic cell or virus, thereby creating said recombinant or synthetic cell or virus comprising a watermark.

Provided herein is a method of creating a recombinant or synthetic cell or virus comprising a watermark, comprising: (i) generating a nucleic acid sequence comprising one or more codon identifiers from a set of human readable symbols of a reference language comprising said watermark that conveys a non-genetic message, wherein a symbol mapping is configured to map a human readable symbol with a frequency of distribution of less than one percent in the set of human readable symbols to a start codon, and wherein the symbol mapping is further configured to map a human readable symbol with a frequency of distribution of more than five percent in the set of human readable symbols to a stop codon; (ii) synthesizing said nucleic acid sequence; and (iii) introducing said nucleic acid sequence into a recombinant or synthetic cell or virus, thereby creating said recombinant or synthetic cell or virus comprising a watermark.

Alternatively, provided herein is a method of creating a recombinant or synthetic cell or virus comprising a watermark, comprising: (i) generating a nucleic acid sequence comprising one or more codon identifiers from a set of human readable symbols of a reference language comprising said watermark that conveys a non-genetic message, wherein a symbol mapping is configured to map a human readable symbol with a frequency of distribution of less than one percent in the set of human readable symbols to a start codon, and wherein the symbol mapping is further configured to map a human readable symbol with a frequency of distribution of more than five percent in the set of human readable symbols to a stop codon; (ii) synthesizing said nucleic acid sequence; and (iii) introducing said nucleic acid sequence into a recombinant or synthetic cell or virus, thereby creating said recombinant or synthetic cell or virus comprising a watermark.

In one embodiment, the symbol mapping does not map a three nucleotide codon identifier to a single letter representation of an amino acid residue normally assigned to that three nucleotide codon in the standard genetic code.

In another embodiment, the generating step (i) is computer-assisted and comprises identifying the set of human readable symbols at a memory module and for each human readable symbol in the set, using a processor to read a symbol mapping for determining a codon identifier which maps to the respective human readable symbol.

Methods of Use

Current technologies allow the generation of synthetic nucleic acid molecules and/or the ability to alter the nucleic acid sequences of existing nucleic acid molecules. With a careful coding scheme and arrangement, it is possible to encode important information as a synthetic nucleic acid sequence and store it in a living host safely and permanently. This technology can be used to identify origins of a host containing a watermark and protect research and development investments. It can also be used in environmental research to track generations of organisms and observe the ecological impact of pollutants. Today, there are microorganisms that can survive under extreme conditions. As well, it is advantageous to consider multicellular organisms as hosts for stored information. These living organisms can provide as memory housing and protection for stored data or information. The present invention provides well for data storage in a living organism wherein at least one non-genetic message or watermark is encoded to represent information and incorporated into a living cell or organism.

One aspect provided herein is the storage of a non-genetic message in multicellular living organisms (e.g., rodents, primates, sheep, horses, cows, pigs, dogs, cats, etc.). This can be achieved by incorporating at least one nucleic acid sequence encoded to represent a non-genetic message into a germ cell; a precursor cell that gives rise to gametes that will then serve as specialized haploid cells (sperm or egg) in sexual reproduction, or stem cell; a relatively undifferentiated cell that will continue dividing indefinitely, throwing off (producing) daughter cells that will undergo terminal differentiation into particular cell types. The encoded nucleic acid sequence will then propagate into a multicellular living organism. This embodiment of the invention is a memory storage system that takes advantage of multicellular organisms (e.g., insect, rodent, etc.) and serves to propagate the encoded nucleic acid sequence in all daughter cells stemming from the original host stem cell.

Also provided herein is a memory storage system wherein a living organism comprises therein at least one nucleic acid sequence encoded to represent a non-genetic message. The stored non-genetic message resides in a living organism and remains there until recovery is desired. The non-genetic message is then retrieved and decoded so as to enable communication. Like a computer memory device that can store data and programs, the same or similar items can be contained in a nucleic acid memory system.

Non-genetic messages or watermarks described herein can be used to trace or monitor distribution of a particular cell or organism in situ, ex situ, in vitro, in vivo, or a combination thereof.

Provided herein is a method of determining the presence of a recombinant or synthetic organism comprising a reference watermark in an sample that conveys a non-genetic message, said method comprising: (i) sequencing nucleic acid material obtained from one or more organisms in said environmental sample; (ii) transforming the nucleic acid sequence obtained in step (i) to a set of codon identifiers, wherein each codon identifier of said set of codon identifiers consists of three nucleotides of said sequence in all three reading frames; (iii) determining a human readable symbol for each codon identifier in the sequence in all three reading frames, wherein said determination is based at least in part upon a symbol mapping that map codons identifiers corresponding to start codon(s) to human readable symbols that possess a disproportionally low frequency in the language of the watermark, and that maps codon identifiers corresponding to stop codon(s) to human readable symbols that possess a disproportionally high frequency in the language of the watermark; and (iv) comparing the human readable symbol sequence of all three reading frames to the reference watermark in said recombinant or synthetic organism, whereby the presence of the reference watermark in any reading frame of the nucleic acid material obtained in step (i) indicates the presence of the recombinant or synthetic organism in the environmental sample.

Provided herein is a method of determining the presence of a recombinant or synthetic organism comprising a reference watermark in an sample that conveys a non-genetic message, said method comprising: (i) sequencing nucleic acid material obtained from one or more organisms in said environmental sample; (ii) transforming the nucleic acid sequence obtained in step (i) to a set of codon identifiers, wherein each codon identifier of said set of codon identifiers consists of three nucleotides of said sequence in all three reading frames; (iii) determining a human readable symbol for each codon identifier in the sequence in all three reading frames, wherein said determination is based at least in part upon a symbol mapping that is configured to map a start codon to a human readable symbol with a frequency of distribution of less than one percent in the set of human readable symbols and is further configured to map a stop codon to a human readable symbol with a frequency of distribution of more than five percent in the set of human readable symbols; and (iv) comparing the human readable symbol sequence of all three reading frames to the reference watermark in said recombinant or synthetic organism, whereby the presence of the reference watermark in any reading frame of the nucleic acid material obtained in step (i) indicates the presence of the recombinant or synthetic organism in the environmental sample.

A sample can be any sample that can contain a recombinant or synthetic cell such as, for example, an environmental sample, a sample deposited with a cell depository (e.g., American Type Culture Collection (ATCC) or another international depository, a laboratory sample, a food supplements, a commercial sample, recombinantly engineered crops and seeds, etc.

Environmental samples include, but are not limited to water samples, soil samples, crops, oil deposits or spills, coal deposits, mineral deposits, algal cells used for biofuel production, recombinantly engineered crops and seeds, crops that have come in contact with recombinantly engineered crops (e.g., corn, grapes, etc.) by virtue of reproduction, samples containing cells or organisms useful for improving soil quality, fungi used to enhance plant growth, etc.

Samples include, but are not limited to, cells and organisms in a research laboratory. Such samples may be distributed internally within a company, university or institute, or distributed externally as part of a collaboration or material transfer agreement.

Samples also include nutritional supplements such as, for example, algae stocks used in nutritional supplements, desiccated algae, bacteria for use in digestive supplements and/or yogurt cultures, animal food and animal supplements.

Samples also include bacterial and viral vaccines such as, for example, live vaccines, modified vaccines, inactivated vaccines, etc.

Also contemplated herein are samples containing organisms for making industrial enzymes. Such enzymes are useful, for example, in commercial detergents (e.g., dish soap, laundry detergent, etc.).

Samples also include recombinantly engineered animals (e.g., rodents, primates, sheep, horses, cows, bulls, pigs, dogs, cats, etc.). Provided herein is a method for genetic tagging of a non-human organism by introducing into the organism a nucleic acid molecule containing a watermark that can be decoded using the methods described herein.
Methods of Monitoring and Tracking In one aspect, provided herein is a method of monitoring the source, ownership, or changes in a sample over time. The sample being monitored can be sample containing one or more of: a prokaryotic cell, a virus, an archaeal cell or a eukaryotic cell. Monitoring can determine whether the state of a sample has been changed over time. For example, a recombinantly engineered crop can be monitored to determine cells containing a modification are spread through the environment via natural means or are transported illegally. Monitoring can be accomplished by any of the methods provided herein.

In another aspect, provided herein is a method of tracking a sample that is transported through either natural or artificial means.

Although embodiments of this application have been described with reference to the accompanying drawings, it is to be noted that various changes and modifications will become apparent to those skilled in the art. Such changes and modifications are to be understood as being included within the scope of embodiments as defined by the appended claims.

Terms and phrases used in this document, and variations thereof, unless otherwise expressly stated, should be construed as open ended as opposed to limiting. As examples of the foregoing, the term "including" should be read as mean "including, without limitation" or the like; the term "example" is used to provide exemplary instances of the item in discussion, not an exhaustive or limiting list thereof; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

EXAMPLES

Elements of the present application are illustrated by the following examples, which should not be construed as limiting in any way.

Example 1

Encoding Methods

FIGS. 3 and 8 identify codon identifiers and the respective symbols encoded therefrom. By virtue of the design of the non-genetic message or watermark, the encoded text does not correspond to the sequences of a gene or other biologically active sequence when in the form of a nucleic acid in the cell or organism. The examples provided in the Figures encode all letters in the American English alphabet as well as all 10 numerals and common punctuation marks.

While the present Figures and Examples are described with respect to the English language, one would comprehend that the coding scheme can be adapted to any reference language as described above.

An encoded non-genetic message in the nucleic acid sequence is flanked by the sequence 5'-TTAACTAGCTAA-3' (SEQ ID NO: 1) on both the 5' and 3' sides of the watermark since that sequence contains a stop codon in all 6 reading frames.

To encode a non-genetic message or watermark, one can substitutes in a serial, one-to-one manner, a given symbol of human readable text using one or more of: the Roman alphabet, Arabic numerals, and certain common punctuation and formatting symbols for strings of three nucleotides. These substitutions are performed such that each successive codon identifier (three nucleotide sequence) is added to the 3' end of the nucleic acid sequence.

For example, the encoding of the text "JCVI-Strain 012.3 All Rights Reserved, 2009." into a nucleic acid sequence watermark can be performed either by hand or by computer program as follows:

First the watermark begins with the DNA sequence 5'-TTAACTAGCTAA-3' (SEQ ID NO: 1). Next, the first human readable symbol of the text is "J". According to the exemplary table above, the letter "J" (either upper or lower case) corresponds to the 3-nucleotide string 5'-GTT-3' in the code. Therefore the next three nucleotides of the watermark are 5'-GTT-3', which are added to the 3' end of the preceding water nark sequence. At this stage the still incomplete watermark's sequence is 5'-TTAACTAGCTAAGTT-3' (SEQ ID NO: 7).

The next human readable symbol of the text is "C" which is corresponds to the 3-nucleotide string 5'-TTT-3' in the code. Therefore the next three nucleotides of the watermark are 5'-TTT-3'. At this stage the still incomplete water nark's sequence is 5'-TTAACTAGCTAAGTTTTT-3' (SEQ ID NO: 8).

In this manner, one serially adds the appropriate three nucleotide strings that correspond to the human readable symbols of the text to the 3' end of the growing watermark sequence. Human readable symbols that are not covered in the code are skipped. When all the human readable symbols of the text have been skipped or encoded into the water nark, the sequence 5'-TTAACTAGCTAA-3' (SEQ ID NO: 1) is added to its 3' end.

Thus, the completely encoded watermark sequence for the text "JCVI-Strain 012.3 All Rights Reserved, 2009." is:

(SEQ ID NO: 9)
5'-
TTAACTAGCTAAGTTTTTTGCTGCCCGCTTGACTATAGCTGTGCATATC
TCTTACTCGAAATATATAGAACAACATACTACTGTACTCATGAGCTATAC
TATAAGCTTAACTATTGTAAATTGTGATAACTTCTTCTGTACGATTAACT
AGCTAA-3'.

Example 2

Decoding Methods

To decode a watermark one performs the same process as encoding as described in Example 1, but in reverse.

One substitutes in a serial one-to-one manner, each successive three nucleotides of the watermark for their respective human readable symbols of human readable text. These substitutions (performed either by hand or by a computer program) are made such that each human readable symbol is placed to the right of the preceding symbol as one substitutes along the watermark in a 5' to 3' direction. This is process of substitution is performed after the sequence 5'-TTAACTAGCTAA-3' (SEQ ID NO: 1) is removed from both ends of the watermark.

For example, to decode the sequence 5'-TTAACTAGCTAAGTTTTTTGCTGCCCGCTTGAC-TATAGCTGTGCATATCTCTTAC TCGAAATATATA-GAACAACATACTACTGTACTCATGAGCTATAC-TATAAGCTTAA CTATTGTAAATTGTGATAACTTCTTCTGTACGAT-TAACTAGCTAA-3' (SEQ ID NO: 9), the first step removes the sequence 5'-TTAACTAGCTAA-3' (SEQ ID NO: 1) from both ends of the watermark leaving the following watermark:

(SEQ ID NO: 10)
5'-
GTTTTTTGCTGCCCGCTTGACTATAGCTGTGCATATCTCTTACTCGAAA
TATATAGAACAACATACTACTGTACTCATGAGCTATACTATAAGCTTAAC
TATTGTAAATTGTGATAACTTCTTCTGTACGA-3'.

Next, the first three nucleotides of the remaining watermark sequence are 5'-GTT-3' which corresponds in the code to the letter "J". Thus, the first letter of the decoded text is "J". The next three nucleotides of the remaining watermark sequence are 5'-TTT-3' which corresponds in the code to the letter "C". Thus the decoded text now reads "JC".

In this manner, one serially substitutes the appropriate human readable symbols that correspond to the three nucleotide strings of the watermark to the right side of the growing decoded text. In this exemplary case, the final decoded watermark reads: "JCVI-STRAIN 012.3 ALL RIGHTS RESERVED, 2009."

When one is unsure of the original reading frame to decode the sequence, this would be performed in all three 5' reading frames; thus beginning the sequence with GTT as the first codon identifier (1), then with TTT as the first codon identifier (2), and then with TTT as the first codon identifier (3) to see if any of these yield a sequence of human readable symbols as follows:

(SEQ ID NO: 11)
GTT TTT TTG CTG CCC GCT . . . (1) = JCVI-S . . .

(SEQ ID NO: 12)
TTT TTT TGC TGC CCG CTT . . . (2) = CCNN(1 . . .

(SEQ ID NO: 13)
TTT TTT GCT GCC CGC TTG . . . (3) = CCS68V . . .

wherein reading frame (1) would emerge as the recognizable sequence of human readable symbols, i.e., the watermark.

The decoded sequence is presented in uppercase letters because the code, in its basic form, does not distinguish between upper and lower case letters, causing the information of which letters were originally capitalized to be lost in the encoding process. However, punctuation marks such as commas, periods, hyphens, and spaces are all retained through the encoding and decoding procedures.

The above example demonstrates one of the useful features of the DNA watermarks: if the above watermark were encoded twice in the same genomic molecule at locations a convenient distance apart from one another (e.g., 2 kilobases) and on opposing strands, a single primer PCR reaction may be used as a diagnostic strain-specific test to identify the molecule in question. In this exemplary case, the primer would have a sequence that would place the 3' end of the primer inside the portion of the watermark that encoded the strain number.

Example 3

Synthetic Cells Containing Watermarks

A 1.08 Mbp *Mycoplasma mycoides* genome was chemically synthesized, and assembled in yeast as a centromeric plasmid; the genome was isolated as naked DNA and transplanted into *Mycoplasma capricolum* to create a new bacterial cell controlled only by the synthetic genome.

Described in International Patent Application PCT/US10/35490 is the design, synthesis and assembly of the 1,077,947-bp *Mycoplasma mycoides* JCVI-syn1 genome from 1,078 1-kb synthetic DNA cassettes. The assembly was facilitated by in vitro and in vivo assembly methods. Cassettes in sets of ten were assembled by yeast recombination and propagated in a yeast/*Escherichia coli* shuttle vector. The 10-kb assemblies were recombined in sets of ten to produce 100-kb assemblies. The resulting eleven 100-kb assemblies were recombined in a single final step into the complete genome. A yeast clone bearing the synthetic genome was selected and confirmed by multiplex PCR and restriction analysis.

The assembled synthetic genome was propagated in yeast as a centromeric plasmid and successfully transplanted into restriction-minus *Mycoplasma capricolum* cells. The new cells have the phenotypic properties expected for *M. mycoides* and the designed synthetic DNA sequence, including watermark sequences and other designed gene deletions and polymorphisms. This strain is referred to as *M. mycoides* JCVI-syn1; this was the second bacterial chromosome synthesized and the first over one million bp. It is a synthetic bacterial genome successfully transplanted into a recipient cell resulting in new cells that are controlled only by a synthetic chromosome. The new synthetic chromosome cells are capable of continuous self-replication. This study confirmed the ability to start with digitized genetic information, synthesize new DNA and transplant that synthetic DNA into cells replacing all of the existing genetic information and, as a result, created new cells controlled only by that synthetic designed DNA. The existing (endogenous) genetic information was lost and as a result new cells were created which were controlled only by the designed synthetic chromosome.

Synthetic Donor Genome Design

Design of the *M. mycoides* JCVI-syn1 genome was based on the highly accurate finished genome sequences of two previously described laboratory strains of *M. mycoides* subspecies capri GM12 (Benders et al., *Nucleic Acids Res*, (2010); Lartigue et al., Science 325, 1693 (2009)). One was the genome donor used by Lartigue et al. [GenBank accession CP001621] (Lartigue et al., *Science* 317, 632 (2007)). The other was a strain created by transplantation of a genome that had been cloned and engineered in yeast, YCpMmyc1.1-ΔtypeIIIres, [GenBank accession CP001668] (Lartigue et al., *Science* 325, 1693 (2009)). Differences at 95 sites were identified between the *M. mycoides* genomic sequences. The sequence of the genome successfully transplanted from yeast (CP001668) was used as a design reference; all differences between previously synthesized cassettes that appeared to be of biological significance were corrected to match CP001668. Sequence differences between our synthetic cassettes and CP001668 that occurred at 19 sites appeared harmless, and so were not corrected. These provided 19 polymorphic differences between the synthetic genome (JCVI-syn1) and the natural genome that we have cloned in yeast and use as a standard for genome transplantation from yeast, YCpMmyc1.1 (Lartigue et al., Science 325, 1693 (2009)).

Watermarks

To differentiate between a synthetic or non-naturally occurring genome and a natural one, four exemplary watermark sequences were designed; these sequences were added to a genome at places where insertion of an additional sequence, or where replacement of a sequence, would not interfere with viability.

Watermark-1, 321 Unencoded Characters, 1246 Base Pairs

J. CRAIG VENTER INSTITUTE 2009
ABCDEFGHIJKLMNOPQRSTUVWXYZ
0123456789#@()-+\=/:<;>$&}{*]"[%!'.,
SYNTHETIC GENOMICS, INC.
<!DOCTYPE HTML><HTML><HEAD><TITLE>GENOME
TEAM</TITLE></HEAD><BODY><A
HREF = "HTTP://WWW.JCVI.ORG/">THE JCVI</A><P>PROVE

-continued

YOU'VE DECODED THIS
WATERMARK BY EMAILING US <A
HREF = "MAILTO:MROQSTI@JCVI.ORG">HERE!</A></P>
</BODY></HTML>

(SEQ ID NO: 14)
TTAACTAGCTAAGTTCGAATATTTCTATAGCTGTACATATTGTAATGCTG

ATAACTAATACTGTGCGCTTGACTGTGATCCTGATAAATAACTTCTTCTG

TAGGGTAGAGTTTTATTTAAGGCTACTACTGGTTGCAAACCAATGCCGTA

CATTACTAGCTTGATCCTTGGTCGGTCATTGGGGGATATCTCTTACTAAT

AGAGCGGCCTATCGCGTATTCTCGCCGGACCCCCCTCTCCCACACCAGCG

GTGTACATCACCAAGAAAATGAGGGGAACGGATGAGGAACGAGTGGGGGC

TCATTGCTGATCATAATGACTGTTTATATACTAATGCCGTCAACTGTTTG

CTGTGATACTGTGCTTTCGAGGGCGGGAGATTCTTTTTGACATACATAAA

TATCATGACAAAACAGCCGGTCATGACAAAACAGCCGGTCATAATAGATT

AGCCGGTGACTGTGAAACTAAAGCTACTAATGCCGTCAATAAATATGATA

ATAGCAACGGCCTGACTGTGAAACTAAAGCCGGCACTCATAATAGATTAG

CCGGAGTCGTATTCATAGCCGGTAGATATCACTATAAGGCCCAGGATCAT

GATGAACACAGCACCACGTCGTCGTCCGAGTTTTTTTGCGCGACGTCTAT

ACCACGGAAGCTGATCATAAATAGTTTTTTTGCTGCGGCACTAGAGCCGG

ACAAGCACACTACGTTTGTAAATACATCGTTCCGAATTGTAAATAATTTA

ATTTCGTATTTAAATTAATGATCACTGGCTATAGTCTAGTGATAACTACA

ATAGCTAGCAATAAGTCATATATAACAATAGCTGAACCTGTGCTACATAT

CCGCTATACGGTAGATATCACTATAAGGCCCAGGACAATAGCTGACTGAC

GTCAGCAACTACGTTTAGCTTGACTGTGGTCGGTTTTTTTGCTGCGACGT

CTATACGGAAGCTCATAACTATAAGAGCGGCACTAGAGCCGGCACACAAG

CCGGCACAGTCGTATTCATAGCCGCACTCATGACAAAACAGC

*GGCGCGCC* TTAACTAGCTAA

Watermark-2 326 Unencoded Characters, 1081 Base Pairs

MIKKEL ALGIRE, MICHAEL MONTAGUE, SANJAY VASHEE,
CAROLE LARTIGUE, CHUCK MERRYMAN, NINA ALPEROVICH,
NACYRA ASSAD-GARCIA, GWYN BENDERS, RAY-YUAN
CHUANG, EVGENIA DENISOVA,DANIEL GIBSON, JOHN
GLASS, ZHI-QING QI.
"TO LIVE, TO ERR, TO FALL, TO TRIUMPH, TO RECREATE
LIFE OUT OF LIFE."-JAMES JOYCE (SEQ ID NO: 15)
TTAACTAGCTAACAACTGGCAGCATAAAACATATAGAACTACCTGCTATA

AGTGATACAACTGTTTTCATAGTAAAACATACAACGTTGCTGATAGTACT

CCTAAGTGATAGCTTAGTGCGTTTAGCTATATTGTAGGCTTCATAATAAG

TGATATTTTAGCTACGTAACTAAATAAACTAGCTATGACTGTACTCCTAA

GTGATATTTTCATCCTTTGCAATACAATAACTACTACATCAATAGTGCGT

GATATCCTGTGCTAGATATAGAACACATAACTACGTTTGCTGTTTTCAGT

GATATGCTAGTTTCATCTATAGATATAGGCTGCTTAGATTCCCTACTAGC

TATTTCTGTAGGTGATATACGTCCATTGCATAATTAATGCATTTAACTAG

CTGTGATACTATAGCATCCCCATTCCTAGTGCATATTTTCATCCTAGTGC

TACGTGATATAATTGTACTAATGCCTGTAGATAAATTTAATGCCTGGCTCG

-continued
TTTGTAGGTGAAATTTAGTGCCTGTAAAACATATACCTGAGTGCTCGTTG

CGTGATAGTTCGTTCATGCATATACAACTAGGCTGCTGTGATATGGTCAC

TGCCCTTACTGTGCTACATATTACTGCGAGGGGGATGACTATAAACCTGT

TGTAAGTGATATGACGTATATAACTACTAGTGATATGACGTATAGGCTAG

AACAACGTGATATGACGTATATGACTACTGTCCCAAACATCAGTGATATG

ACGTATACTATAATTTCATAATAGTGATAAATAAACCTGGGCTAAATACG

TTCCTGAATACGTGGCATAAACCTGGGCTAACGAGGAATACCCATAGTTT

AGCAATAAGCTATAGTTCGTCATTTTTAA*GGCGCGCC*TTAACTAGTAA

Watermark-3 335 Unencoded Characters, 1109 Base Pairs

CLYDE HUTCHISON, ADRIANA JIGA, RADHA KRISHNAKUMAR,
JAN MOY, MONZIA MOODIE, MARVIN FRAZIER, HOLLY
BADEN-TILSON, JASON MITCHELL, DANA BUSAM, JUSTIN
JOHNSON, LAKSHMI DEVI VISWANATHAN, JESSICA
HOSTETLER, ROBERT FRIEDMAN, VLADIMIR NOSKOV,
JAYSHREE ZAVERI.
"SEE THINGS NOT AS THEY ARE, BUT AS THEY MIGHT
BE."
                                        (SEQ ID NO: 16)
TTAACTAGCTAATTTAACCATATTTAAATATCATCCTGATTTTCACTGGC

TCGTTGCGTGATATAGATTCTACTGTAGTGCTAGATAGTTCTGTACTAGG

TGATACTATAGATTTCATAGATAGCACACTGGCTTCATGCTAGGCATCCC

AATAGCTAGTGATAGTTTAGTGCATACAACGTCATGTGATACAACGTTGC

TGGCTGTAGATACAACGTCGTATTCTGTAAGTGATACAATAGCTATTGCT

GTGCAAGGCCTATAGTGGCTGTAACTAGTGATATCACGTAACAACCATAT

AAGTTAGATTTAATGCCCCTGACTGAACGCTCGTTGCGTGATAGTTTAGG

CTCGTTGCATACAACTGTGATTTTCATAAAACACGTGATAATTTAGTGCT

AGATAAGTTCCGCTTAGCAAGTGATAGTTTCCGCTTGACTGTGCATAGTT

CGTTCATGCGCTCGTTGCGTGATAAACTAGGCAGCTTCACAACTGATAAT

TTAATTGCTGAATTGCTGGCTGTCTAGTGCTAGTGATCATAGTGCGTGAT

AGTTTAAGCTGCTCTGTTTTAGATATCACGTGCTTGATAATGAAACTAAC

TAGTGATACTACGTAGTTAACTATGAATAGGCCTACTGTAATTCAATAGT

GCGTGATATTGAACTAGATTCTGCAACTGCTAATATGCCGTGCTGCACGT

TTGGTGATAGTTTAGCATGCTTCACTATAATAAATATGGTAGTTGTAACT

ACTGCGAATAGGGGGAGTTAATAAATATGATCACTGTGCTACGCTATATG

CCGTTGAATATAGGCTATATGATCATAACATATATAGCTATAAGTGATAA

GTTCCTGAATATAGGCTATATGATCATAACATATACAACTGTACTATGAA

TAAGTTAACGAGGATTAACTAGCTAA

Watermark-4 338 Unencoded Characters, 1222 Base Pairs

CYNTHIA ANDREWS-PFANNKOCH, QUANG PHAN, LI MA,
HAMILTON SMITH, ADI RAMON, CHRISTIAN TAGWERKER, J
CRAIG VENTER, EULA WILTURNER, LEI YOUNG, SHIBU
YOOSEPH, PRABHA IYER, TIM STOCKWELL, DIANA RADUNE,
BRIDGET SZCZYPINSKI, SCOTT DURKIN, NADIA FEDOROVA,
JAVIER QUINONES, HANNA TEKLEAB.
"WHAT I CANNOT BUILD, I CANNOT UNDERSTAND."-
RICHARD FEYNMAN

-continued
                                        (SEQ ID NO: 17)
TTAACTAGCTAATTTCATTGCTGATCACTGTAGATATAGTGCATTCTATA

AGTCGCTCCCACAGGCTAGTGCTGCGCACGTTTTTCAGTGATATTATCCT

AGTGCTACATAACATCATAGTGCGTGAAAACCTGATACAATAGGTGATAT

CATAGCAACTGAACTGACGTTGCATAGCTCAACTGTGATCAGTGATATAG

ATTCTGATACTATAGCAACGTTGCGTGATATTTTCACTACTGGCTTGACT

GTAGTCATATGATAGTACGTCTAACTAGCATAACTAGTGATAGTTATATT

TCTATAGCTGTACATATTGTAATGCTGATAACTAGTGATATAATCCAACT

AGATAGTCCTGAACTGATCCCTATGCTAACTAGGATAAACTAACTGATAC

ATCGTTCCTGCTACGTGATAGCTTCACTGAGTTCCATACATCGTCGTGCT

TAAACATCAGTGATAACACTATAGAGTTCATAGATACTGCATTAACTAGT

GATATGACTGCAATAGCTTGACGTTTTGCAGTCTAAAACAACGTGATAAT

TCTGTAGTGCTAGATACTATAGATTTCCTGCTAAGTGATAAGTCTACTGA

TTTACTAATGAATAGCTTGGTTTTGGCATACACTGTGCGTGCACTGGTGA

TAGCTTTTCGTTGATGAATAATTTCCCTAGCACTGTGCGTGATATGCTAG

ATTCTGTAGATAGGCTAAATTCGTCTACGTTTGTAGGTGATAGTTTAGTT

GCTGTAACTAATATTATCCTGTGCCGTTGCTAAGCTGTGATATCATAGTG

CTGCTAGATATGATAAGCAAACTAATAGAGTCGAGGGGGAGTCTCATAGT

GAATACTGATATTTTAGTGCTGCCGTTGAATAAGTTCCCTGAACATGTGA

TACTGATATTTTAGTGCTGCCGTTGAATATCCTGCATTTAACTAGCTTGA

TAGTGCATTCGAGGAATACCCATACTACTGTTTTCATAGCTAATTATAGG

CTAACATTGCCAATAGTGC*GGCGGCC*TTAACTAGCTAA

Watermarks 1-4 replaced cassettes 282-287, 447, 106, and 680, respectively as previously described in PCT/US10/35490. The watermarks were inserted in regions experimentally demonstrated (watermarks 1 (1246 bp) and 2 (1081 bp)) or predicted (watermarks 3 (1109 bp) and 4 (1222 bp) to not interfere with cell viability. An all-6 reading frame stop codon is underlined at the beginning and end of each watermark; Afc I restriction sites are shown in bold italics. Since data indicated that the genome sequence represented by cassettes 936-939 was dispensable, a version of cassette 940 that contained an 80 bp overlap to cassette 935 was produced. This would produce a 4-kb deletion and further distinguish the synthetic genome from a natural one.

The synthetic genome design, with this deletion and the four watermark sequences was 1,077,947 bp in length. This sequence was partitioned into cassettes 1,080 bp in length with 80 bp overlaps, and a NotI restriction site (GCGGC-CGC) was added to each end. A map of the genes, the 1,078 cassettes from which it was assembled, expected polymorphisms, unexpected polymorphisms an inserted E. coli transposon, and other features of M. mycoides JCVI-syn1 was created which provides the genome map of M. mycoides JCVI-syn1. Genes, structural RNAs, watermarks, polymorphisms relative to natural. M. mycoides capri GM12, and the coordinates of the synthetic DNA cassettes were identified.

Synthetic Donor Genome Assembly and Transplantation

A hierarchical strategy was designed to assemble the genome in 3 stages by transformation and homologous recombination in yeast. In the first stage, cassettes were taken 10-at-a-time to produce 10 kb assembly intermediates. In the second stage, these 10 kb intermediates were taken 10-at-a-time to produce eleven ~100 kb assembly intermediates. In the final stage, all 11 DNA fragments were assembled into a complete synthetic genome.

In order to further enrich for the eleven circular assembly intermediates, ~200 ng samples of each assembly were pooled and mixed with molten agarose. As the agarose solidifies, the fibers thread through and topologically "trap" circular DNA (Dean et al., *Anal Biochem* 56, 417 (December, 1973)).

Untrapped linear DNA can then be electrophoresed out of the agarose plug, thus enriching for the trapped circular molecules. The eleven circular assembly intermediates were digested with NotI so that the inserts could be released. Subsequently, the fragments were extracted from the agarose plug, analyzed by FIGE (data not shown), and transformed into yeast spheroplasts. In this third and final stage of assembly, an additional vector sequence was not required since the yeast propagation elements were already present in assembly 811-900. Following incubation on selective plates, approximately 100 colonies appeared.

Topological trapping and analysis was conducted. Yeast cultures (50 ml) were grown and processed as previously described. Yeast clones containing a completely assembled synthetic genome were screened by multiplex PCR with a primer set that produces 11 amplicons; one at each of the 11 assembly junctions. Primer pairs were designed to span each of the eleven 100-kb assembly junctions. Of 48 colonies screened, DNA extracted from one clone (sMmYCp235) produced all 11 amplicons. PCR of the WT positive control (YCpMmyc1.1) produced an indistinguishable set of 11 amplicons (data not shown).

To further demonstrate the complete assembly of a synthetic *M. mycoides* genome, intact DNA was isolated from yeast in agarose plugs and subjected to two restriction analyses; AscI and BssHII. Since these restriction sites are present in three of the four watermark sequences, this choice of digestion produces restriction patterns that are distinct from the natural *M. mycoides* genome. Natural (WT) and synthetic (235) *M. mycoides* genomes were isolated from yeast in agarose plugs. In addition, DNA was purified from the host strain alone. Agarose plugs were digested with AscI or BssHII and fragments were separated by clamped homogeneous electrical field (CHEF) gel electrophoresis.

Transplantation of Synthetic Donor Genome into Recipient Cells

Additional agarose plugs used in the gel analysis above were also used in genome transplantation experiments. Intact synthetic *M. mycoides* genomes from the sMmYCp235 yeast clone were transplanted into restriction-minus *M. capricolum* recipient cells, as previously described (Lartigue et al., *Science* 325, 1693 (Sep. 25, 2009)). Results were scored by selecting for growth of blue colonies on SP4 medium containing tetracycline and X-gal at 37° C. Genomes isolated from this yeast clone produced 5-15 tetracycline-resistant blue colonies per agarose plug. This was comparable to the YCpMmyc1.1 control. Recovery of colonies in all transplantation experiments was observed when both *M. capricolum* recipient cells and an *M. mycoides* genome were present.

To rapidly distinguish the synthetic transplants from *M. capricolum* or natural *M. mycoides*, two analyses were performed. First, four primer pairs that were specific to each of the four watermarks were designed such that they produce four amplicons in a single multiplex PCR reaction.

Transplants containing a synthetic genome were screened by multiplex PCR with a primer set that produces 4 amplicons; one internal to each of the four watermarks. One transplant (syn1) originating from yeast clone sMmYCp235 was analyzed alongside a natural, non-synthetic genome (WT) transplanted out of yeast.

All four amplicons were produced by transplants generated from sMmYCp235, but not YCpMmyc1.1 (data not shown).

Second, the gel analysis with AscI and BssHII, described above, was performed. Briefly, natural (WT) and synthetic (syn1) *M. mycoides* genomes were isolated from *M. mycoides* transplants in agarose plugs. Agarose plugs were digested with AscI or BssHII and fragments were separated by CHEF gel electrophoresis. The restriction pattern obtained was consistent with a transplant produced from a synthetic *M. mycoides* genome (data not shown).

A single transplant originating from the sMmYCp235 synthetic genome was sequenced. With the exception of the known polymorphisms that occurred during the synthesis process, and 8 new polymorphisms and an unexpected *E. coli* transposon insertion, the sequence matched the intended design. This strain is referred to as *M. mycoides* JCVI-syn1. Colonies (i.e., growing, dividing cells) were grown on SP4 agar containing Xgal to make the cells expressing beta-galactosidase blue. Thus, synthetic cells comprising four watermarks that did not biologically impact the viability of the cells had been produced.

While preferred embodiments have been shown and described herein, such embodiments are provided by way of example only. It should be understood that various alternatives and equivalents to the embodiments described herein can be employed.

What is claimed is:

1. A method of generating a sequence of codon identifiers corresponding to a sequence of human readable symbols, and assigned according to a coding scheme to convey a non-genetic message in a human reference language, the method comprising:
   (i) receiving the sequence of human readable symbols at a memory module;
   (ii) loading a human readable symbol map within the memory module, wherein the human readable symbol map is configured to map human readable symbols as follows:

| | | | | | |
|---|---|---|---|---|---|
| GGA = " | GAA = ' | TTC = # | CAG = : | TGT = ; | ACG = [ |
| AGG = ] | AAA = { | AAG = } | CCG = ( or ) | GAC = ( or ) | CGG = < |
| AGC = > | CAC = / | CTC = \ | CGA = . | GTG = , | CCC = - |
| CCT = + | CCA = = | TCG = @ | ATC = $ | GAT = % | GAG = ! |
| ACC = & | ATG = * | ATA = space | GGG = new line | | |
| TCT = 0 | CTT = 1 | ACT = 2 | AAT = 3 | AGA = 4 | GCG = 5 |
| GCC = 6 | TAT = 7 | CGC = 8 | GTA = 9 | | |
| TAG = A | AGT = B | TTT = C | ATT = D | TAA = E | GGC = F |
| TAC = G | TCA = H | CTG = I | GTT = J | GCA = K | AAC = L |
| CAA = M | TGC = N | CGT = O | ACA = P | TTA = Q | CTA = R |
| GCT = S | TGA = T | TCC = U | TTG = V | GTC = W | GGT = X |
| CAT = Y | TGG = Z | | | | | and
   (iii) using a transcoder to map a sequence of codon identifiers corresponding to each human readable symbol within the sequence according to the human readable symbol map and outputting the sequence,
   (iv) synthesizing a nucleic acid with the sequence of step (iii).

2. The method of claim 1 wherein said set of human readable symbols comprises a watermark that allows the authentication or identification of said recombinant or synthetic organism comprising said watermark.

3. The method of claim 2 wherein said watermark is a copyright notice, a trademark, a company identifier, a name, a phrase, a sentence, a quotation, genetic information, unique identifying information, data, or a combination of any thereof.

4. The method of claim 1 wherein the synthetic nucleic acid sequence further comprises an all-6 reading frame stop codon containing sequence 5' to a first codon identifier in the sequence and/or an all-6 reading frame stop codon containing sequence 3' to the last codon identifier in the sequence.

5. An apparatus for transforming a sequence of codon identifiers into a nucleic acid sequence of claim 1, the apparatus comprising:
   (i) a processor adapted to execute instructions; and
   (ii) a storage module, wherein the storage module comprises a data structure for mapping codon identifiers into human readable symbols, and a set of instructions that are executed by the processor and generate a human readable symbol for each codon identifier read from a sequence of codon identifiers, wherein the human readable symbol generated is based at least in part upon the data structure; wherein the data structure is configured to map human readable symbols as follows:

| | | | | | |
|---|---|---|---|---|---|
| GGA = " | GAA = ' | TTC = # | CAG = : | TGT = ; | ACG = [ |
| AGG = ] | AAA = { | AAG = } | CCG = ( or ) | GAC = ( or ) | CGG = < |
| AGC = > | CAC = / | CTC = \ | CGA = . | GTG = , | CCC = - |
| CCT = + | CCA = = | TCG = @ | ATC = $ | GAT = % | GAG = ! |
| ACC = & | ATG = * | ATA = space | GGG = new line | | |
| TCT = 0 | CTT = 1 | ACT = 2 | AAT = 3 | AGA = 4 | GCG = 5 |
| GCC = 6 | TAT = 7 | CGC = 8 | GTA = 9 | | |
| TAG = A | AGT = B | TTT = C | ATT = D | TAA = E | GGC = F |
| TAC = G | TCA = H | CTG = I | GTT = J | GCA = K | AAC = L |
| CAA = M | TGC = N | CGT = O | ACA = P | TTA = Q | CTA = R |
| GCT = S | TGA = T | TCC = U | TTG = V | GTC = W | GGT = X |
| CAT = Y | TGG = Z. | | | | |

6. The apparatus of claim 5, wherein the data structure or mapping function, respectively, does not map a codon identifier to a single letter representation of an amino acid residue normally assigned to that codon identifier in the standard genetic code.

7. The apparatus of claim 5, wherein the sequence of codon identifiers comprises an all-6 reading frame stop codon containing sequence 5' to a first codon identifier in the sequence and/or an all-6 reading frame stop codon containing sequence 3' to the last codon identifier in the sequence.

* * * * *